(12) United States Patent
Ayyavoo et al.

(10) Patent No.: US 7,151,172 B1
(45) Date of Patent: Dec. 19, 2006

(54) **ATTENUATED *VIF* DNA IMMUNIZATION CASSETTES FOR GENETIC VACCINES**

(75) Inventors: Velpandi Ayyavoo, Monroeville, PA (US); Thanadavarayan Nagashunmugam, Monroeville, PA (US); David B. Weiner, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/486,625

(22) PCT Filed: Sep. 18, 1998

(86) PCT No.: PCT/US98/19478

§ 371 (c)(1),
(2), (4) Date: Sep. 13, 2000

(87) PCT Pub. No.: WO99/13896

PCT Pub. Date: Mar. 25, 1999

Related U.S. Application Data

(60) Provisional application No. 60/060,172, filed on Sep. 26, 1997.

(51) Int. Cl.
| | |
|---|---|
| C07H 21/04 | (2006.01) |
| C07K 1/00 | (2006.01) |
| C12N 15/00 | (2006.01) |
| C12N 5/10 | (2006.01) |
| C12P 21/06 | (2006.01) |
| A61K 31/70 | (2006.01) |

(52) U.S. Cl. ............... 536/23.72; 530/350; 435/320.1; 435/69.1; 435/325; 514/44

(58) Field of Classification Search ............... 530/350, 530/826; 424/204.1, 188.1, 199.1, 208.1; 536/23.1, 23.72; 435/320.1, 69.1
See application file for complete search history.

(56) References Cited

U.S. PATENT DOCUMENTS

| | | | |
|---|---|---|---|
| 4,945,050 A | 7/1990 | Sanford et al. | 435/172.1 |
| 5,036,006 A | 7/1991 | Sanford et al. | 435/170.1 |
| 5,589,466 A | 12/1996 | Felgner et al. | 514/44 |
| 5,593,972 A | 1/1997 | Weiner et al. | 514/44 |

FOREIGN PATENT DOCUMENTS

| | | |
|---|---|---|
| WO | WO 90/11092 | 10/1990 |
| WO | WO 93/17706 | 9/1993 |
| WO | WO 93/23552 | 11/1993 |
| WO | WO 94/16737 | 8/1994 |
| WO | WO 95/05851 | 3/1995 |

OTHER PUBLICATIONS

Ma et al. Journal of Virology. 1994; 68 (3): 1714-1720.*

Ayyavoo V, et al. "Develpoment of genetic vaccines for pathogenic genes: construction of attenuated vif DNA immunization cassettes", *Aids*, 1997, 11, pp. 1433-1444.

Kim, J. J. et al. "Development of a multicomponent candidate vaccine for HIV-1", *Vaccine*, 1997, 15(8), pp. 879-883.

Miller, R. H. et al. "HIV accessory proteins as therapeutic targets", *Nature Medicine*, 1997, 3(4), pp. 389-394.

Aldrovandi, et al., "Replication and Pathogenicity of Human Immunodeficiency Virus Type 1 Acessory Gene Mutants in SCID-hu Mice", *J. Virology*, 1996, vol. 70, No. 3, pp. 1505-1511.

Ameisen, et al., "Antibody Response to the HIV-1 Regulatory GEI Products NEF, VIF, and VPR in HIV-1 Infectious Seronegative Individuals," *Int Conf. AIDS*, 1989, vol. 5, p. 533.

Ayyavoo, et al., "Analysis of Genetic Heterogeneity, Antigenicity, and Biological Characteristics of HIV-1 in a Maternal Transmitter and Nontransmitter Patient Pair," *DNA and Cell Biology*, 1996, vol. 15, No. 7, pp. 571-580.

Arya et al., "Three Novel Genes of Human T-lymphotropic Virus Type III: Immune Reactivity of their Products with Sera from Acquired Immune Deficiency Syndrome Patients," *Proc. Natl. Acad. Sci. USA*, 1986, vol. 83, pp. 2209-2213.

Blanc et al., "Transcomplementation of VIF- HIV-1 Mutants in CEM Cells Suggests That VIF Affects Late Steps of the Viral Life Cycle," *Virology.*, 1993, vol. 193, pp. 186-192.

Borman et al., "Human Immunodeficiency Virus Type 1 Vif-Mutant Particles from Restrictive Cells: Role of Vif in Correct Particle Assembly and Infectivity," *J. Virol*, 1995, vol. 69, No. 4, pp. 2058-2067.

Cullen et al., "Regulatory Pathways Governing HIV-1 Replication," *Cell*, 1989, vol. 58, pp. 423-426.

Desrosiers, "HIV with Multiple Gene Deletions as a Live Attenuated Vaccine for AIDS," *AIDS Res. AndHuman Retroviruses*, 1992, vol. 8, No. 3, pp. 411-421.

Dougherty et al., "Determination of the Rate of Base-Pair Substitution and Insertion Mutations in Retrovirus Replication," *J. Virol*, 1988, vol. 62, No. 8, pp. 2817-2822.

Fisher et al., "Biologically Diverse Molecular Variants Within a Single Hiv-1 Isolate," *Nature*, 1988, vol. 334, pp. 444-447.

Fynan et al., "Dna Vaccines: Protective Immunization by Parenteral, Mucosal, and Gene-gun Inoculations," *Proc. Natl. Acad. Sci. USA*, 1993, vol. 90, pp. 11478-11482.

Gabuzda et al., "Role of *vif* in Replication of Human Immunodeficiency Virus Type 1 in CD4+ T Lymphocytes," *J. Virol*, 1992, vol. 66, No. 11, pp. 6489-6495.

Garrett et al., "Rev Activates Expression of the Human Immunodeficiency Virus Type 1 *vif* and *vpr* Gene Products," *J. Virol*, 1992, vol. 65, No. 3, pp. 1653-1657.

(Continued)

*Primary Examiner*—Mary E. Mosher
*Assistant Examiner*—Bo Peng
(74) *Attorney, Agent, or Firm*—Cozen O'Connor, P.C.

(57) ABSTRACT

The present invention is directed to nucleic acid molecules encoding attenuated, non-functional virion infectivity factor (vif) proteins. The nucleic acid molecules of the invention are inserted into recombinant expression vectors and administered to mammals in order to induce a cellular and humoral immune response to the encoded protein product.

21 Claims, 17 Drawing Sheets

OTHER PUBLICATIONS

Gibbs et al., "Construction and In Vitro Properties of HIV-1 Mutants with Deletions in "Nonessential" Genes," *Aids Res. And Human Retroviruses*, 1994, vol. 10, No. 4, pp. 343-350.

Goncalves et al., "Subcellular Localization of the Vif Protein of Human Immunodeficiency Virus Type 1," *J. Virol*, 1994, vol. 68, No. 2, pp. 704-712.

Guy et al., "A Specific Inhibitor of Cysteine Proteases Impairs a Vif-Dependent Modification of Human Immunodeficiency Virus Type 1 Env Protein," *J. Virol*, 1991, vol. 65, No. 3, pp. 1325-1331.

Hevey et al., "Complementation of Human Immunodeficiency Virus Type 1 vif Mutants in Some CD4+ T-Cell Lines," *Virus Res*, 1994, vol. 33, pp. 269-280.

Kan et al., "Identification of HTLV-III/LAV sor Gene Product and Detection of Antibodies in Human Sera," *Science*, 1986, vol. 231, pp. 1553-1555.

Lamhamedi et al., "Qualitative and Quantitative Analysis of Human Cytotoxic T-lymphocyte Responses to HIV-1 Proteins," *AIDS*, 1992, vol. 6, No. 11, pp. 1249-1258.

Ma et al, "Cysteine Residues in the Vif Protein of Human Immunodeficiency Virus Type 1 Are essential for Viral Infectivity," *J. Virol*, 1994, vol. 68, No. 3, pp. 1714-1720.

Mahalingam et al., "The Carboxy-Terminal Domain is Essential for Stability and Not for Virion Incorporation of HIV-1 Vpr into Virus Particles," *Virol*, 1995, vol. 214, pp. 647-652.

Meyerhans et al., "Temporal Fluctuations in HIV Quasispecies in Vivo Are Not Reflected by Sequential HIV Isolations," *Cell*, 1989, vol. 58, pp. 901-910.

Michael et al., "Defective Accessory Genes in a Human Immunodeficiency Virus Type 1-Infected Long-Term Survivor Lacking Recoverable Virus," *J. Virol*, 1995, vol. 69, No. 7, pp. 4228-4236.

Nagashunmugam et al., "Cell-Free HIV-1$_{Zr6}$ vif Mutants Are Defective in Binding to Peripheral Blood Mononuclear Cells and in Internalization," *DNA Cell Biol.*, 1996, vol. 15, No. 5, pp. 353-361.

Oberste et al., "Conservation of Amino Acid Sequence Motifs in Lentivirus Vif Proteins," *Virus Gene*, 1992, vol. 6, No. 1, pp. 95-102.

Pircher et al., "Viral Escape by Selection of Cytotoxic T Cell-Resistant Virus Variants *in Vivo,*" *Nature*, 1985, vol. 346, pp. 629-633.

Ratner et al., "Complete Nucleotide Sequence of the AIDS Virus, HTLV-III," *Nature*, 1985, vol. 313, pp. 277-284.

Sakai et al., "Cell Dependent Requirement of Human Immunodeficiency Virus Type 1 Vif Protein for Maturation of Virus Particles," *J. Virol*, 1993, vol. 67, No. 3, pp. 1663-1666.

Schwartz et al., "Expression of Human Immunodeficiency Virus Type 1 vif and vpr mRNAs Is Rev-dependent and Regulated by Splicing," *Virol*, 1991, vol. 183, pp. 677-686.

Schwander et al., "Prevalance of Antibodies to Recombinant Virion Infectivity Factor in the Sera of Prospectively Studied Patients with HIV-1 Infection," *J. of Medical Virol*, 1992, vol. 36, pp. 142-146.

Shackett et al., "Analysis of the vif Gene of Feline Immunodeficiency Virus," *Virol*, 1994, vol. 204, pp. 860-867.

Sodroski et al., "Replicative and Cytopathis Potential of HTLV-III/LAV with *sor* Gene Deletions," *Science*, 1986, vol. 231, pp. 1549-1553.

Sova et al., "Conservation of an Intact Human immunodeficiency Virus Type-1 vif gene In Vitro and In Vivo," *J. Virol*, vol. 69, No. 4, pp. 2557.

Srinivasan et al., "Molecular Characterization of Human Immunodeficiency Virus from Zaire: Nucleotide Sequence Analysis Identifies Conserved and Variable Domains in the Envelope Gene," *Gene*, 1987, vol. 52, pp. 71-82.

Tang et al., "Genetic Immunization is a Simple Method for Eliciting an Immune Response," *Nature*, 1992, vol. 356, pp. 152-154.

Trono., "HIV Accessory Proteins: Leading Roles for the Supporting Cast," *Cell*, 1995, vol. 82, pp. 189-192.

Ulmer et al., "Heterologous Protection Against Influenza by injection of DNA Encoding a Viral Protein," *Science*, 1993, vol. 259, pp. 1745-1749.

Volsky et al., "the Human Immunodeficiency Virus Type 1 *vif* Gene: The Road from an Accessory to an Essential Role in Human Immunodeficiency Virus Type 1 Replication," *Curr. Topics Micro. Immunol.*, 1995, vol. 193, pp. 157-168.

von Schwedler et al., "*vif* Is Crucial for Human Immunodeficiency Virus Type 1 Proviral DNA Synthesis in Infected Cells," *J. Virol.*, 1993, vol. 67, No. 8, pp. 4945-4955.

Wang et al., "Gene Inoculation Generates Immune Responses Against Human Immunodeficiency Virus Type 1," *Proc. Natl. Acad. Sci. USA*, 1993, vol. 90, pp. 4156-4160.

Wang et al., "DNA Inoculation Induces Neutralizing Immune Responses Against Human Immunodeficiency Virus Type 1 in Mice Nonhuman Primates," *DNA And Cell Biol.*, 1993, vol. 12, No. 9, pp. 799-805.

Wang et al., "Nucleic acid-based Immunization Aganist HIV-1 Induction of Protective *in vivo* Immune Responses," *AIDS*, 1995, vol. 9 (Suppl. A), pp. S159-S170.

Wolfs et al., "Naturally Occurring Mutations within HIV-1 V3 Genomic RNA Lead to Antigenic Variation Dependent on a Single Amino Acid Substitution," *Virol.*, 1991, vol. 185, pp. 195-205.

Wieland et al., "In Vivo Genetic Variability of the HIV-1 vif Gene," *Virol.*, 1994, vol. 203, pp. 43-51.

Wieland et al., "Antigenic Domains of the HIV-1 *vif* Protein as Recognized by Human Sera and Murine Monoclonal Antibodies," *AIDS Res. Human. Retrovir.*, 1991, vol. 7, No. 11, pp. 861-867.

Yang et al., "Phosphorylation of Vif and Its Role in HIV-1 Replication," *J. Biol. Chem.*, 1996, vol. 271, No. 17, pp. 10121-10129.

\* cited by examiner

FIGURE 1

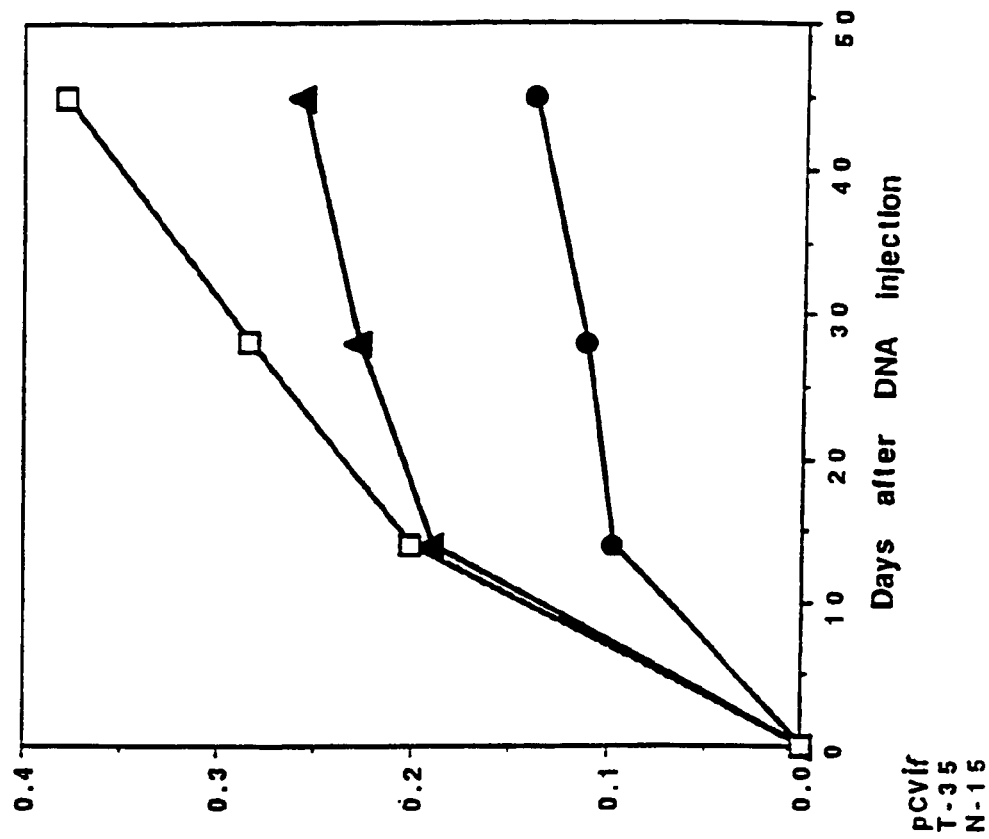
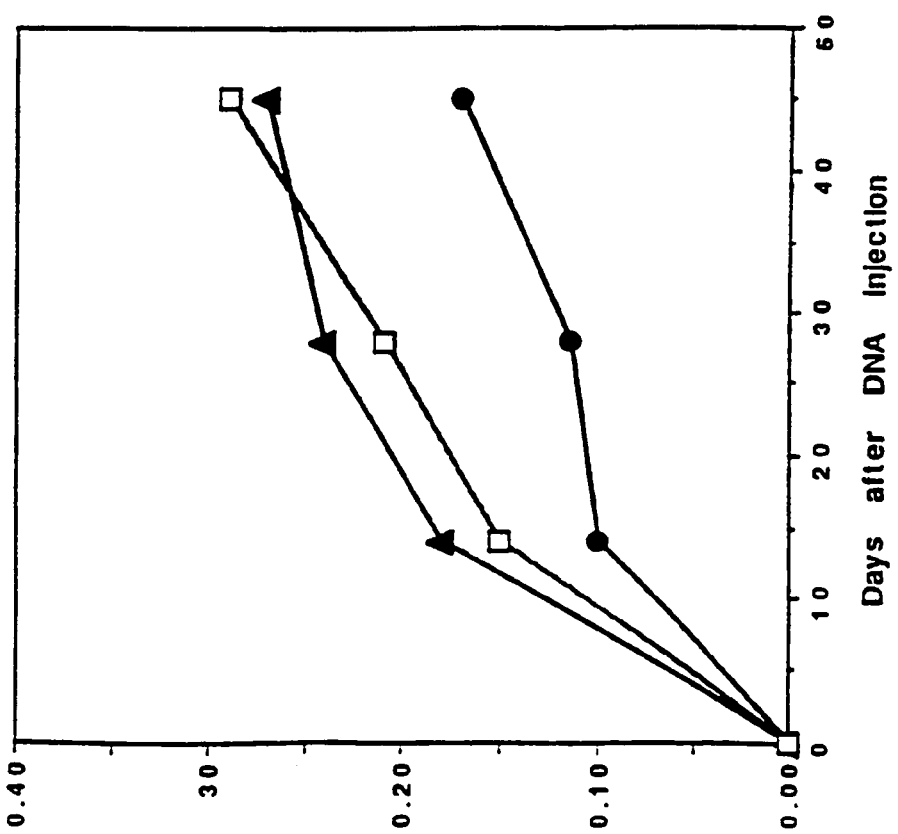
FIGURE 3A
FIGURE 3B

FIGURE 7A

1. Vif-N13.pep

MENRWQVIIV WQVDRMRIRT WNSLVKYHMY *SKKAREWFY *HHYQSPHPK

VSSEVHIPLE DARLEITSFW GLHTGERDWH LGQGVSIEWR KRRYSTHVDP

DLADQLIHLY YFDCFSESAI RKAILGHRVS PRCEYRAGHS KVGSLQYLAI

AALITPKKIK PPLASVRKLT EDRWNKPQKT KGHRGSHIMN GH*

2. Vif-N15.pep

MENRWQVMIV WQVDRMRIRT WNSLVKYHMY RSKKAREWFY RHHYQSPHPR

VSSEVHIPLE DARLEITTYW GLHTGERDWH LGQGVSIEWR KRRYSTQVDP

DLADQLIHLY YFDCFSESAI RKAILGHRVS PRCEYRAGHS KVGSLQYLAI

AALITPKKIK PPLPSVRKLT EDRWNKPQKT KGHRGSHIMN GH*

3. Vif-N17.pep

MENRWQVMIV WQVDRMRIRT WNSLVKYHMY RSKKAREWFY RHHYQSPHPK

VSSEVHIPLE DARLEITTYW GLHTGERDWH LGQGVSIEWR KRRYSTQVDP

DLADQLIHLY YFDCFSESAI RKAILGHRVS PRCEYRAGHS KVGSLQYLAI

AALITPKKIK PPLPSVRKLT EDRWNKPQKT KGHRGSHIMN GH*

FIGURE 7B

4. Vif-N22.pep

MENRWQVMIV WQVDRMRIRT WNSLVTYHMY RSQKAREWFN RHHYHSPHPK

VSSEVHIPLE DARLAIPTFW GLHTGERDWH LQQGVSIEWR KRRYSTQVDP

DLADQLIHLY YFDCFSESAI RKAILGHRVS PRCEYRAGHS KVGSLQYLAL

AALITPKKIK PPLPSVRKLT EDRWNKPQKT KGHRGSHIMN GH*

5. Vif-N24.Pep

MENRWQVMIV WQVDRMRIRT WNSLVKYHMY RSKKAREWFY RHHYQSPHPK

VSSEVHIPLE DARLVITTYW GLHTGERDWH LQQGVSIEWR KRRYSTHVDP

DLADQLIHLY YFDCFSESAI RKAILGHRVS PRCEYRAGHS KVGSLQYLAL

AALITPKKIK PPLASVRKLT EDRWNKPQKT KGHRGSHIMN GH*

6. Vif-N26.pep

MENRWQVMIV WQVDRMRIRT WNSLVKYHMY RSKKAREWFY RHHYQSPHPK

VSSEVHIPLE DARLVITTYW GLHTGERDWH LQQGVSIEWR KRRYSTQVDP

DLADHLIHLY YFDCFSESAI RKAILGHRVS PRCEYRAGHS KVGSLQYLAL

AALITPKKIK PPLASVRKLT EDRWNKPQKT KGHRGSHIMN GH*

7. Vif-N27.pep

MENRWQVMIV WQVDRMRIRT WNSLVKYHMY RSKKAREWFY RHHYQSPHPK

VSSEVHIPLE DARLVITTFW GLHTGERDWH LQQGVSIEWR KRRYSTHVDP

DLADQLIHLY YFDCFSESAI RKAILGHRVS PRCEYRAGHS KVGSLQYLAL

FIGURE 7C

AALITPKKIK PPLPSVRKLT EDRWNKPQKT KGHRGSHIMN GH*

8. Vif-N29.pep

MENRWQVMIV WQVDRMRIRT WNSLVKYHMY RSKKAREWFN RHHYHRPHFK

VSSEVHIPLE DARLEITTFW GLHTGERDWH LGQGVSIEWR KRRYSTQVDP

DLADQLIHLY YFDCFSESAI RKAILGHRVS PRCEYRAGHS KVGSLQYLAI

AALITPKKIK PPLPSVRKLT EDRWNKPQKT KGHRGSHIMN GH*

9. Vif-N30.

MENRWQVMIV WQVDRMRIRT WNSLVKYHMY RSQKEREWFN RHHYHSPHPE

QSSTAHIPLV DGRLEKIAVW SLDTGEGVWH RGHRVSIEWR KRRYSTQVDP

DLVDQLIHLY YFDCFSESAI RKAILGHRVS PRCEYRAGHS KVGSLQYLAI

AALITPKKIK PPLPSVRKLT EDRWNKPQKT KGHRGSHIMN GH*

Vif-T3.pep

MENRWQVMIV WQVDRMRIRT WNSLVKHHMY VSKKAKKWFY RHHYESPHPK

VSSTAHIPLG DGRLEKTAVW SLQAGDGVWH RGHPVSIEWR KRRYSTQVDP

DLVDQLIHLY YFDCFSESAI RKAILGYRVS PRCEYQAGHN KVGSLQYLAL

AALITPKKIK PPLPSVRKLT EDRWNKPQKT KGHRGSHIMN GH*

FIGURE 7D

MENRWQVMIV WQVDRMRIRA WNSLVKHHIY FSKKAKKWFY RHHYESPHPN

VSSEVHIPLG DARLVTTPYW GLHGGERDWY LAQGVSIEWR KRRYSTQVDP

DLADQLIHLY YFDCFSESAI RKAILGYRVS PRCEYQAGHN KVGSLQYLAL

AALITPKKIK PPLPSVRKLT EDRWNKPQKT KGHRGSHIMN GH*

Vif-T37.pep

MENRWEVMIV WEVDRMRIRA WNSLVKHHMY VSKKAKKWFY RHHYESPHPK

VSSEVHIPLG DARLVTTTYW GLHAGERDWH LGQGVSIEWR KRRYSTQVDP

DLADQLIHLY YFDCFSESAI RKAILGYRVS PRCEYQAGHN KVGSLQYLAL

AALITPKKIK PPLPSVRKLT EDRWNKPQKT KGHRGSHIMN GH*

Vif-T38.pep

MENRWQVMIV WQVDRMRIRA WNSLVKHHMY VSKNAKKWFY RHHYDSPHPV

QSSTAHIPLG DGRLQKIAFW SLDAGERDWH LGQGVSIEWR KRRYSTQVDP

DLADQLIHLY YFDCFSESAI RKAILGYRVS PRCEYQAGHN KVGSLQYLAL

AALITPKKIK PPLPSVRKLT EDRWNKPQKT KGHRGRHIMN GH*

Vif-T39.pep

MENRWQVMIV WQVDRMRIRA WNSLVKHHMY VSKKAKKWFY RHHYDSPHPK

VSSEVHIPLG DARLETTTYW GLHAGERDWH LGQGVSIEWR KRRYSTHVDP

FIGURE 7E

DLADQLIHLY YFDCFSESAI RKAILGYRVS PRCEYQAGHN KVGSLQYLAL

AALITPKKIK PPLPSVRKLT EDRWNKPQKT KGHRGSHIMN GH*

Vif-T4.pep

MENRWQVMIV WQVDRMRIRA WNSLVKHHMY VSKKARIWFS RHHYGSPHPK

VCSEVHIPLG DARLVITTYW SLHAGE*DWH VGQRVSIEWR KRRYSTQVDP

DLADQLIHLY YFDCFSESAI RKAILGYRVS PRCEYQAGHN KVGSLQYLAL

AALITPKKIK PPLPSVRKLT EDRWNKPQKT KGHRGSHIMN GH*

Vif-T40.pep

MENRWQVMIV WQVDRMTIRA WNSLVKHHMY VSKKAKKWFY RHHYESPHPK

VSSEVHIPLG DARLVITTYW GLHAGERDWH LGQGVSIEWR KRRYSTQVDP

DLADQLTHLY YFDCFSESAI RKAILGYRVS PRCEYQAGHN KVGSLQYLAL

AALITPKKIK PPLPSVRKLT EDRWNKPQKT KGHRGSHIMN GH*

Vif-T42.pep

MENRWQVMIV WQVDRMRIRA WNSLVKHHMY VSKKAKKWFN RHHYDRPHPK

VSSEVHIPLG DARLETTTFW GLHAGERDWH LGQRVSIEWR KRRYSTQVDP

DLADQLTHLY YFDCFSESAI RKAILGYRVS PRCEYQAGHN KVGSLQYLAL

AALITPKKIK PPLPSVRKLT EDRWNKPQKT KGTEGAIQ*

FIGURE 7F

Vif-T43.pep

MENRWQVMIV WQVDRMRIRA WNSLVKHHMF VSKKAKKWFY RHHYESPHPK

VSSEVHIPLG DARLEITTFW GLHAGERDWH LGQGVSIEWR KRRYSTQVDP

DLADQLIHLY YFGCFSESAI RKAILGYRVS PRCEYQAGHN KVGSLQYLGL

AALITPKKIK PPLPSVRKLT EDRWNKPQKT KGHRGSHIMN GH*

Vif-T44.pep

MENRWQVMIV WQVDRMRIRA WNSLVKHHMY VSKKAKKWFY RHHYESPHPQ

VSSEVHIPLG DARLEITTYW GLHAGERDWH LGQGVSIEWR KRRYSTQVDP

DLADQLIHLY YFDCFSESAI RKAILGYRVS PRCEYQAGHN KVGSLQYLAL

AALITPKKIK PPLPSVRKLT EDRWNKPQKT KGHRGSHIMN GH*

FIGURE 8A

N13 (SEQ ID NO:27)

ATGGAAAACAGATGGCAGGTGATTATTGTGTGGCAGGTAGACAGGATGAGGATTAGAACA
TGGAACAGTTTAGTAAAATACCATATGTATTGATCAAAGAAAGCTAGGGAATGGTTTTAT
TGACATCACTATCAAAGTCCTCATCCAAAAGTAAGTTCAGAAGTACACATCCCACTAGAG
GATGCTAGATTGGAAATAACATCATTTTGGGGTCTGCATACAGGAGAAAGAGACTGGCAT
TTGGGTCAGGGAGTCTCCATAGAATGGAGGAAAAGGAGATATAGCACACACGTCGACCCT
GATCTAGCAGACCAACTAATTCATCTGTATTATTTTGATTGTTTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGGCGAGTGTCAGGAAACTGACAGAGGATAGATGGAACAAGCCCCAGAAGACC
AAGGGCCACAGAGGGAGCCATACAATGAATGGACACTAG

N15 (SEQ ID NO:28)

ATGGAAAACAGATGGCAGGTGATGATTGTGTGGCAGGTAGACAGGATGAGGATTAGAACA
TGGAACAGTTTAGTAAAATACCATATGTATAGATCAAAGAAAGCTAGGGAATGGTTTTAT
AGACATCACTATCAAAGTCCTCATCCAAGAGTAAGTTCAGAAGTACACATCCCACTAGAG
GATGCTAGATTGGAAATAACAACATATTGGGTCTGCATACAGGAGAAAGAGACTGGCAT
TTGGGTCAGGGAGTCTCCATAGAATGGAGGAAAAGGAGATATAGCACACAAGTAGACCCT
GATCTAGCAGACCAACTAATTCATCTGTATTATTTTGATTGTTTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGCCGAGTGTCAGGAAACTGACAGAGGATAGATGGAACAAGCCCCAGAAGACC
AAGGGCCACAGAGGGAGCCATACAATGAATGGACACTAG

N17 (SEQ ID NO:29)

ATGGAAAACAGATGGCAGGTGATGATTGTGTGGCAGGTAGACAGGATGAGGATTAGAACA
TGGAACAGTTTAGTAAAATACCATATGTATAGATCAAAGAAAGCTAGGGAATGGTTTTAT
AGACATCACTATCAAAGTCCTCATCCAAAAGTAAGTTCAGAAGTACACATCCCACTAGAG
GATGCTAGATTGGAAATAACAACATATTGGGTCTGCATACAGGAGAAAGAGACTGGCAT
TTGGGTCAGGGAGTCTCCATAGAATGGAGGAAAAGGAGATATAGCACACAAGTAGACCCT
GATCTAGCAGACCAACTAATTCATCTGTATTATTTTGATTGTTTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGCCGAGTGTCAGGAAACTGACAGAGGATAGATGGAACAAGCCCCAGAAGACC
AAGGGCCACAGAGGGAGCCATACAATGAATGGACACTAG

N22 (SEQ ID NO:30)

ATGGAAAACAGATGGCAGGTGATGATTGTGTGGCAGGTAGACAGGATGAGGATTAGAACA
TGGAACAGTTTAGTAACATACCATATGTATAGATCACAGAAAGCTAGGGAATGGTTTAAT
AGACATCACTATCACAGTCCTCATCCAAAAGTAAGTTCAGAAGTCCACATCCCACTAGAG
GATGCTAGATTGGCAATACCAACATTTTGGGGTCTGCATACAGGAGAAAGAGACTGGCAT
TTGGGTCAGGGAGTCTCCATAGAATGGAGGAAAAGGAGATATAGCACACAAGTAGACCCT
GATCTAGCAGACCAACTAATTCATCTGTATTATTTTGATTGTTTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGCCGAGTGTCAGGAAACTGACAGAGGATAGATGGAACAAGCCCCAGAAGACC
AAGGGCCACAGAGGGAGCCATACAATGAATGGACACTAG

FIGURE 8B

N23 (SEQ ID NO:31)

ATGGAAAACAGATGGCAGGTGATGATTGTGTGGCAGGTAGACAGGATGAGGATTAGAACA
TGGAACAGTTTAGTAAAATACCATATGTATAGATCAAAGAAAGCTAGGGAATGGTTTTAT
AGACATCACTATCAAAGTCCTCATCCAAAAGTAAGTTCAGAAGTCCACATCCCACTAGAG
GATGCTAGATTGGAAATAACAACATATTGGGGTCTGCATACAGGAGAAAGAGACTGGCAT
TTGGGTCAGGGAGTCTCCATAGAATGGAGGAAAAGGAGATATAGCACACACGTCGACCCT
GATCTCGCAGACCACCTAATTCATCTGTGTTATTTTGATTGTCTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGCCGAGTGTCAGGAAACTGACAGAGGATAGATGGAACAAGCCCCAGAAGACC
AAGGGCCACAGAGGGAGCCATACAATGAATGGACACTAG

N24 (SEQ ID NO:32)

ATGGAAAACAGATGGCAGGTGATGATTGTGTGGCAGGTAGACAGGATGAGGATTAGAACA
TGGAACAGTTTAGTAAAATACCATATGTATAGATCAAAGAAAGCTAGGGAATGGTTTTAT
AGACATCACTATCAAAGTCCTCATCCAAAAGTAAGTTCAGAAGTACACATCCCACTAGAG
GATGCTAGATTGGTAATAACAACATATTGGGGTCTGCATACAGGAGAAAGAGACTGGCAT
TTGGGTCAGGGAGTCTCCATAGAATGGAGGAAAAGGAGATATAGCACACACGTAGACCCT
GATCTAGCAGACCAACTAATTCATCTGTATTATTTTGATTGTTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGGCGAGTGTCAGGAAACTGACAGAGGATAGATGGAACAAGCCCCAGAAGACC
AAGGGCCACAGAGGGAGCCATACAATGAATGGACACTAG

N26 (SEQ ID NO:33)

ATGGAAAACAGATGGCAGGTGATGATTGTGTGGCAGGTAGACAGGATGAGGATTAGAACA
TGGAACAGTTTAGTAAAATACCATATGTATAGATCAAAGAAAGCTAGGGAATGGTTTTAT
AGACATCACTATCAAAGTCCTCATCCAAAAGTAAGTTCAGAAGTACACATCCCACTAGAG
GATGCTAGATTGGTAATAACAACATATTGGGGTCTGCATACAGGAGAAAGAGACTGGCAT
TTGGGTCAGGGAGTCTCCATAGAATGGAGGAAAAGGAGATATAGCACACAAGTAGACCCT
GATCTAGCAGACCACCTAATTCATCTGTATTATTTTGATTGTTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGGCGAGTGTCAGGAAACTGACAGAGGATAGATGGAACAAGCCCCAGAAGACC
AAGGGCCACAGAGGGAGCCATACAATGAATGGACACTAG

N27 (SEQ ID NO:34)

ATGGAAAACAGATGGCAGGTGATGATTGTGTGGCAGGTAGACAGGATGAGGATTAGAACA
TGGAACAGTTTAGTAAAATACCATATGTATAGATCAAAGAAAGCTAGGGAATGGTTTTAT
AGACATCACTATCAAAGTCCTCATCCAAAAGTAAGTTCAGAAGTACACATCCCACTAGAG
GATGCTAGATTGGTAATAACAACATTTTGGGGTCTGCATACAGGAGAAAGAGACTGGCAT
TTGGGTCAGGGAGTCTCCATAGAATGGAGGAAAAGGAGATATAGCACACACGTAGACCCT
GATCTAGCAGACCAACTAATTCATCTGTATTATTTTGATTGTTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGCCGAGTGTCAGGAAACTGACAGAGGATAGATGGAACAAGCCCCAGAAGACC
AAGGGTCACAGAGGGAGCCATACAATGAATGGACACTAG

FIGURE 8C

N29 (SEQ ID NO:35)

ATGGAAAACAGATGGCAGGTGATGATTGTGTGGCAGGTAGACAGGATGAGGATTAGAACA
TGGAACAGTTTAGTAAAATACCATATGTATAGATCAAAGAAAGCTAGGGAATGGTTTAAT
AGACATCACTATCACCGTCCTCATCCAAAAGTAAGTTCAGAAGTCCACATCCCACTAGAG
GATGCTAGATTGGAAATAACAACATTTTGGGGTCTGCATACAGGAGAAAGAGACTGGCAT
TTGGGTCAGGGAGTCTCCATAGAATGGAGGAAAAGGAGATATAGCACACAAGTAGACCCT
GATCTAGCAGACCAACTAATTCATCTGTATTATTTTGATTGTTTTCAGAATCTGCTATA
AGAAAAGCCATATTAGGACACAGAGTTAGTCCTAGGTGTGAATATCGAGCAGGACATAGC
AAGGTAGGATCACTACAGTACTTGGCAATAGCAGCATTAATAACACCAAAAAAGATAAAG
CCACCTTTGCCGAGTGTCAGGAAACTGACAGAGGATAGATGGAACAAGCCCCAGAAGACC
AAGGGCCACAGAGGGAGCCATACAATGAATGGACACTAG

N30 (SEQ ID NO:36)

ATGGAAAACAGATGGCAGGTGATGATTGTGTGGCAGGTAGACAGGATGAGGATTAGAACA
TGGAACAGTTTAGTAAAATACCATATGTATTGATCAAAGAAAAGAAAGAAAGGGAATGGT
TTTATAGACATCACTATCACAGCCCTCATCCAGAACAAAGTTCAACAGCCCACATCCCGC
TAGTGGATGGTAGATTGGAAAAAATAGCAGTTTGGAGTCTGGATACAGGAGATGGCGTCT
GGCACAGGGGGCATCGAGTCTCCATAGAATGGAGGAAAAGGAGATATAGCACACAAGTAG
ACCCTGATCTAGTAGACCAACTAATTCATCTGTATTATTTTGATTGTTTTTCAGAATCTG
CTATAAGAAAAGCCATATTAGGACACAGAGTTAGTCCTAGGTGTGAATATCGAGCAGGAC
ATAGCAAGGTAGGATCACTACAGTACTTGGCAATAGCAGCATTAATAACACCAAAAAAGA
TAAAGCCACCTTTGCCGAGTGTCAGGAAACTGACAGAGGATAGATGGAACAAGCCCCAGA
AGACCAAGGGCCACAGAGGGAGCCATACAATGAATGGACACTAG

T3 (SEQ ID NO:37)

ATGGAAAACAGATGGCAGGTGATGATTGTGTGGCAAGTAGACAGGATGAGGATTAGAACA
TGGAACAGTTTAGTAAAACACCATATGTATGTTTCAAAGAAAGCTAAGAAATGGTTTTAT
AGACATCACTATGAAAGCCCTCATCCAAAAGTAAGTTCAACAGCCCACATCCCGCTAGGG
GATGGTAGATTGGAGAAAACAGCAGTTTGGAGTCTGCAGGCAGGAGATGGAGTCTGGCAC
AGGGGGCATCCAGTCTCCATAGAATGGAGGAAAAGGAGATATAGCACACAAGTAGACCCT
GATTTGGTAGACCAACTAATTCATCTGTATTATTTTGATTGTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTTAGGAAACTGACAGAGGATAGATGGAACAAGCCCCAGAAGACC
AAGGGCCACAGAGGGAGCCATACAATGAATGGACACTAG

T4 (SEQ ID NO:38)

ATGGAAAACAGATGGCAGGTGATGATTGTGTGGCAAGTAGACAGGATGAGGATTAGAGCA
TGGAACAGTTTAGTAAAACACCATATGTATGTTTCAAAGAAAGCTAGGACATGGTTTTCT
AGACATCACTATGGAAGCCCTCATCCAAAAGTATGTTCAGAAGTACACATCCCACTAGGG
GATGCTAGATTGGTGATAACAACATATTGGAGTCTGCATGCAGGAGAATGAGACTGGCAT
GTGGGTCAGAGAGTCTCCATAGAATGGAGGAAAAGGAGATATAGCACACAAGTAGACCCT
GACTTGGCAGACCAACTAATTCATCTGTATTATTTTGATTGTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTGAGGAAACTGACAGAGGATAGATGGAACAAGCCCCAGAAGACC
AAGGGCCACAGAGGGAGCCATACAATGAATGGACACTAG

FIGURE 8D

T35 (SEQ ID NO:39)

ATGGAAAACAGATGGCAGGTGATGATTGTGTGGCAAGTAGACAGGATGAGGATTAGAGCA
TGGAACAGTTTAGTAAAACACCATATTTATTTTCAAAGAAAGCTAAGAAATGGTTTTAT
AGACATCACTATGAAAGCCCTCATCCAAACGTAAGTTCAGAAGTACACATCCCACTAGGG
GATGCTAGATTGGTGACAACACCATATTGGGGTCTGCATGGAGGAGAAAGAGACTGGTAT
CTGGCTCAGGGAGTCTCCATAGAATGGAGGAAAAGGAGATATAGCACACAAGTAGACCCT
GACCTGGCAGACCAACTAATTCATCTGTATTATTTTGATTGTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTGAGGAAACTGACAGAGGATAGATGGAACAAGCCCCAGAAGACC
AAGGGCCACAGAGGGAGCCATACAATGAATGGACACTAG

T37 (SEQ ID NO:40)

ATGGAAAACAGATGGGAGGTGATGATTGTGTGGGAAGTAGACAGGATGAGGATTAGAGCA
TGGAACAGTTTAGTAAAACACCATATGTATGTTTCAAAGAAAGCTAAGAAATGGTTTTAT
AGACATCACTATGAAAGCCCTCATCCAAAAGTAAGTTCAGAAGTACACATCCCACTAGGG
GATGCTAGATTGGTGATAACAACATATTGGGGTCTGCATGCAGGAGAAAGAGACTGGCAT
TTGGGTCAGGGAGTCTCCATAGAATGGAGGAAAAGGAGATATAGCACACAAGTAGACCCT
GACCTGGCAGACCAACTAATTCATCTGTATTATTTTGATTGTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTGAGGAAACTGACAGAGGATAGATGGAACAAGCCCCAGAAGACC
AAGGGCCACAGAGGGAGCCATACAATGAATGGACACTAG

T38 (SEQ ID NO:41)

ATGGAAAACAGATGGCAGGTGATGATTGTGTGGCAAGTAGACAGGATGAGGATTAGAGCA
TGGAACAGTTTAGTAAAACACCATATGTATGTTTCAAAGAACGCTAAGAAATGGTTTTAT
CGACATCACTATGACAGCCCTCATCCAGTCCAAAGTTCAACAGCCCACATCCCGCTAGGG
GATGGTAGATTGCAGAAAATAGCATTTGGAGTCTGGATGCAGGAGAAAGAGACTGGCAT
TTGGGTCAGGGAGTCTCCATAGAATGGAGGAAAAGGAGATATAGCACACAAGTAGACCCT
GACCTGGCAGACCAACTAATTCATCTGTATTATTTTGATTGTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTGAGGAAACTGACAGAGGATAGATGGAACAAGCCCCAGAAGACC
AAGGGGCACAGAGGGAGGCATACAATGAATGGACACTAG

T39 (SEQ ID NO:42)

ATGGAAAACAGATGGCAGGTGATGATTGTGTGGCAAGTAGACAGGATGAGGATTAGAGCA
TGGAACAGTTTAGTAAAACACCATATGTATGTTTCAAAGAAAGCTAAGAAATGGTTTTAT
AGACATCACTATGACAGCCCTCATCCAAAAGTAAGTTCAGAAGTACACATCCCACTAGGG
GATGCTAGATTGGAGATAACAACATATTGGGGTCTGCATGCAGGAGAAAGAGACTGGCAT
TTGGGTCAGGGAGTCTCCATAGAATGGAGGAAAAGGAGATATAGCACACACGTAGACCCT
GACCTGGCAGACCAACTAATTCATCTGTATTATTTTGATTGTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTGAGGAAACTGACAGAGGATAGATGGAACAAGCCCCAGAAGACC
AAGGGCCACAGAGGGAGCCATACAATGAATGGACACTAG

FIGURE 8E

T40 (SEQ ID NO:43)

ATGGAAAACAGATGGCAGGTGATGATTGTGTGGCAAGTAGACAGGATGACGATTAGAGCA
TGGAACAGTTTAGTAAAACACCATATGTATGTTTCAAAGAAAGCTAAGAAATGGTTTTAT
AGACATCACTATGAAAGCCCTCATCCAAAAGTAAGTTCAGAAGTACACATCCCACTAGGG
GATGCTAGATTGGTGATAACAACATATTGGGGTCTGCATGCAGGAGAAAGAGACTGGCAT
TTGGGTCAGGGAGTCTCCATAGAATGGAGGAAAAGGAGATATAGCACACAAGTAGACCCT
GACTTGGCAGACCAACTAACTCATCTGTATTATTTTGATTGTTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTGAGGAAACTGACAGAGGATAGATGGAACAAGCCCCAGAAGACC
AAGGGCCACAGAGGGAGCCATACAATGAATGGACACTAG

T42 (SEQ ID NO:44)

ATGGAAAACAGATGGCAGGTGATGATTGTGTGGCAAGTAGACAGGATGAGGATTAGAGCA
TGGAACAGTTTAGTAAAACACCATATGTATGTTTCAAAGAAAGCTAAGAAATGGTTTAAT
AGACATCACTATGACCGCCCTCATCCAAAAGTAAGTTCAGAAGTCCACATCCCACTAGGG
GATGCTAGATTGGAGATAACAACATTTGGGGTCTGCATGCAGGAGAAAGAGACTGGCAT
TTGGGTCAGCGAGTCTCCATAGAATGGAGGAAAAGGAGATATAGCACACAAGTAGACCCT
GACTTGGCAGACCAACTAACTCATCTGTATTATTTTGATTGTTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTGAGGAAACTGACAGAGGATAGATGGAACAAGCCCCAGAAGACC
AAGGGCACAGAGGGAGCCATACAATGAATGGACACTAG

T43 (SEQ ID NO:45)

ATGGAAAACAGATGGCAGGTGATGATTGTGTGGCAAGTAGACAGGATGAGGATTAGAGCA
TGGAACAGTTTAGTAAAACACCATATGTTTGTTTCAAAGAAAGCTAAGAAATGGTTTTAT
AGACATCACTATGAAAGCCCTCATCCAAAAGTAAGTTCAGAAGTACACATCCCACTAGGG
GATGCTAGATTGGAGATAACAACATTTTGGGGTCTGCATGCAGGAGAAAGAGACTGGCAT
TTGGGTCAGGGAGTCTCCATAGAATGGAGGAAAAGGAGATATAGCACACAAGTAGACCCT
GACCTGGCAGACCAACTAATTCATCTGTATTATTTTGGTTGTTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGGACTAGCAGCATTAATAACACCAAAGAAGATAAAG
CCACCTTTGCCTAGTGTGAGGAAACTGACAGAGGATAGATGGAACAAGCCCCAGAAGACC
AAGGGCCACAGAGGGAGCCATACAATGAATGGACACTAG

T44 (SEQ ID NO:46)

ATGGAAAACAGATGGCAGGTGATGATTGTGTGGCAAGTAGACAGGATGAGGATTAGAGCA
TGGAACAGTTTAGTAAAACACCATATGTATGTTTCAAAGAAAGCTAAGAAATGGTTTTAT
AGACATCACTATGAAAGCCCTCATCCACAAGTAAGTTCAGAAGTACACATCCCACTAGGG
GATGCTAGATTGGAGATAACAACATATTGGGGTCTGCATGCAGGAGAAAGAGACTGGCAT
TTGGGTCAGGGAGTCTCCATAGAATGGAGGAAAAGGAGATATAGCACACAAGTAGACCCT
GACCTGGCAGACCAACTAATTCATCTGTATTATTTTGATTGTTTTTCAGAATCTGCTATA
AGAAAAGCCATATTAGGATATAGAGTTAGTCCTAGGTGTGAATACCAAGCAGGACATAAT
AAGGTAGGATCTCTACAGTACTTGGCACTAGCAGCATTAATAACACCAAAGAAGATAAAG
CCACCTTTGCCTAGTGTGAGGAAACTGACAGAGGATAGATGGAACAAGCCCCAGAAGACC
AAGGGCCACAGAGGGAGCCATACAATGAATGGACACTAG

ATTENUATED *VIF* DNA IMMUNIZATION CASSETTES FOR GENETIC VACCINES

This application is a 371 of PCT International Application No. PCT/US98/19478, filed Sep. 18, 1998 and claims benefit of 60/060,172, filed Sep. 26, 1997.

ACKNOWLEDGMENT OF GOVERNMENT RIGHTS

This invention was made with Government support from the National Institutes of Health. The Government has certain rights in this invention.

FIELD OF THE INVENTION

The invention relates to the preparation and use of attenuated, nonfunctional HIV vif immunization cassettes as genetic vaccines for pathogenic genes.

BACKGROUND OF THE INVENTION

Vaccination and immunization generally refer to the introduction of a non-virulent agent against which an individual's immune system can initiate an immune response which will then be available to defend against challenge by a pathogen. The immune system identifies invading "foreign" compositions and agents primarily by identifying proteins and other large molecules which are not normally present in the individual. The foreign protein represents a target against which the immune response is made.

The immune system can provide multiple means for eliminating targets that are identified as foreign. These means include humoral and cellular responses which participate in antigen recognition and elimination. Briefly, the humoral response involves B cells which produce antibodies that specifically bind to antigens. There are two arms of the cellular immune response. The first involves helper T cells which produce cytokines and elicit participation of additional immune cells in the immune response. The second involves killer T cells, also known as cytotoxic T lymphocytes (CTLs), which are cells capable of recognizing antigens and attacking the antigen including the cell or particle it is attached to.

Vaccination has been singularly responsible for conferring immune protection against several human pathogens. In the search for safe and effective vaccines for immunizing individuals against infective pathogenic agents such as viruses, bacteria, and infective eukaryotic organisms, several strategies have been employed thus far. Each strategy aims to achieve the goal of protecting the individual against pathogen infection by administering to the individual, a target protein associated with the pathogen which can elicit an immune response. Thus, when the individual is challenged by an infective pathogen, the individual's immune system can recognize the protein and mount an effective defense against infection. There are several vaccine strategies for presenting pathogen proteins which include presenting the protein as part of a non-infective or less infective agent or as a discreet protein composition.

One strategy for immunizing against infection uses killed or inactivated vaccines to present pathogen proteins to an individual's immune system. In such vaccines, the pathogen is either killed or otherwise inactivated using means such as, for example, heat or chemicals. The administration of killed or inactivated pathogen into an individual presents the pathogen to the individual's immune system in a noninfective form and the individual can thereby mount an immune response against it. Killed or inactivated pathogen vaccines provide protection by directly generating T-helper and humoral immune responses against the pathogenic immunogens. Because the pathogen is killed or otherwise inactivated, there is little threat of infection.

Another method of vaccinating against pathogens is to provide an attenuated vaccine. Attenuated vaccines are essentially live vaccines which exhibit a reduced infectivity. Attenuated vaccines are often produced by passaging several generations of the pathogen through a permissive host until the progeny agents are no longer virulent. By using an attenuated vaccine, an agent that displays limited infectivity may be employed to elicit an immune response against the pathogen. By maintaining a certain level of infectivity, the attenuated vaccine produces a low level infection and elicits a stronger immune response than killed or inactivated vaccines. For example, live attenuated vaccines, such as the poliovirus and smallpox vaccines, stimulate protective T-helper, T-cytotoxic, and humoral immunities during their nonpathogenic infection of the host.

Another means of immunizing against pathogens is provided by recombinant vaccines. There are two types of recombinant vaccines: one is a pathogen in which specific genes are deleted in order to render the resulting agent non-virulent. Essentially, this type of recombinant vaccine is attenuated by design and requires the administration of an active, non-virulent infective agent which, upon establishing itself in a host, produces or causes to be produced antigens used to elicit the immune response. The second type of recombinant vaccine employs infective non-virulent vectors into which genetic material that encode target antigens is inserted. This type of recombinant vaccine similarly requires the administration of an active infective non-virulent agent which, upon establishing itself in a host, produces or causes to be produced, the antigen used to elicit the immune response. Such vaccines essentially employ infective non-virulent agents to present pathogen antigens that can then serve as targets for an anti-pathogen immune response. For example, the development of vaccinia as an expression system for vaccination has theoretically simplified the safety and development of infectious vaccination strategies with broader T-cell immune responses.

Another method of immunizing against infection uses subunit vaccines. Subunit vaccines generally consist of one or more isolated proteins derived from the pathogen. These proteins act as target antigens against which an immune response may be mounted by an individual. The proteins selected for subunit vaccine are displayed by the pathogen so that upon infection of an individual by the pathogen, the individuals immune system recognizes the pathogen and mounts a defense against it. Because subunit vaccines are not whole infective agents, they are incapable of becoming infective. Thus, they present no risk of undesirable virulent infectivity that is associated with other types of vaccines. It has been reported that recombinant subunit vaccines such as the hepatitis B surface antigen vaccine (HBsAg) stimulate a more specific protective T-helper and humoral immune response against a single antigen. However, the use of this technology to stimulate board protection against diverse pathogens remains to be confirmed.

The construction of effective vaccines is complicated by several factors which include the pathobiology of the pathogen and the specificities of the of the host immune response. Recently a novel tool for understanding the immune component in these interactions has become available in the form of genetic immunization or DNA vaccination. Tang, et al., *Nature,* 1992, 356, 152; Fynan, et al., *Proc. Natl. Acad. Sci. USA,* 1993, 90, 11478; Ulmer, et al., *Science,* 1993, 259, 1745; and Wang, et al., *Proc. Natl. Acad. Sci. USA,* 1993, 90, 4156. The ability of this approach was demonstrated to produce broad immune responses against structural and enzymatic gene products of HIV-1 and outlined a strategy for development of a possible prophylactic vaccine for HIV-1. This strategy utilized multiple gene expression cassettes encoding gag/pol/rev as well as env/rev and accessory gene immunogens. Studies clearly demonstrated that rodents and primates can be successfully immunized with HIV-1 structural and envelope genes. Wang, et al., *Proc. Natl. Acad. Sci. USA,* 1993, 90, 4156 and Wang, et al., *DNA Cell Biol.,* 1993, 12, 799. A genetic strategy for construction of immunogen expression cassettes from a pathogenic gene which can be broadly applied in order to use DNA immunogens against a variety of pathogens is needed.

Primate lentiviral genomes contain genes encoding novel regulatory and accessory proteins as well as proteins with structural and enzymatic functions. The regulatory genes, tat and rev, and the accessory genes, nef, vif, vpr, vpu, and vpx, are well conserved in many lentiviruses, including HIV and SIV. The well conserved nature of these genes implies that their protein products play a critical role in viral pathogenesis in vivo. Initial in vitro experiments seemed to demonstrate that tat and rev were essential for viral replication, while the accessory genes were considered nonessential. Cullen, et al., *Cell,* 1989, 58, 423 and Desrosiers, *AIDS Res. Human Retroviruses,* 1992, 8, 411. Further analyses, however, has revealed that defects within the accessory gene result in severe impairment or delay in viral replication in vitro (Gabudza, et al, *J. Virol.,* 1992, 66, 6489 and Gibbs, et al., *AIDS Res. Human Retroviruses,* 1994, 10, 343) and in vivo (Aldrovandi, et al., *J. Virol.,* 1996, 70, 1505). Native defective accessory genes have been reported in vivo and may be an end product of an effective host immune response. The accessory genes are, therefore, presently considered to be determinants of virus virulence. Trono, *Cell,* 1995, 82, 189. They contain few "hot spots" and may be less susceptible to mutations leading to the production of "escape" virus variants, emphasizing their importance in the viral life cycle. In addition, the protein products of these genes are immunogenic in vivo. As a group, they represent twenty percent of the possible anti-viral immune targets. Ameisen, et al., *Int. Conf. AIDS,* 1989, 5, 533 and Lamhamedi-Cherradi, et al., *AIDS,* 1992, 6, 1249. Their immunogenicity and low functional mutagenicity combine to make the accessory genes attractive elements in the design of future anti-viral immune therapeutics. The production of accessory gene immunogens poses specific immunologic and pathogenic complications for a viral vaccine design, however, due to the role of the accessory gene protein products as determinants of viral virulence. A potential accessory gene-based genetic vaccine would need to be accessible to the host's immune response against native viral accessory gene products without enhancing viral replication. Accordingly, a major goal is to design a safe and effective genetic anti-HIV vaccine, which includes the vif (virion infectivity factor) accessory gene as part of a multi-component genetic immunogen.

The vif gene encodes a 23 kDa late viral protein (vif) from a singly spliced, rev-dependent 5 kb transcript. Arya, et al., *Proc. Natl. Acad. Sci. USA,* 1986, 83, 2209; Garrett, et at, *J. Virol.,* 1991, 65, 1653; Schwartz, et al., *Virol.,* 1991, 183, 677; and Sodroski, et al., *Science,* 1986, 231, 1549. Vif is highly conserved among HIV-1 isolates and is present in other lentiviruses, such as Feline Immunodeficiency Virus (FIV), Bovine Immunodeficiency Virus (BIV), Visna virus, HIV-2, and SIV. Myers, et al., *Human Retrovir. AIDS,* 1991 and Shackett, et al., *Virol.,* 1994, 204, 860. Earlier analyses of in vivo vif genetic variation have shown that most vif sequences are intact reading frames and the presence of intact vif does not have a correlation with disease status. Sova, et al, *J. Virol.,* 1995, 69, 2557 and Wieland, et al., *Virol.,* 1994, 203, 43. However, sequential analyses of a region containing vif, vpr, vpu, tat, and rev genes from a HIV-1 infected long-term progressor revealed the presence of inactivating mutations in 64% of the clones. Michael, et al., *J. Virol.,* 1995, 69, 4228. HIV-1 infected subjects have been shown to carry antibodies which recognize recombinant vif protein (Kan, et al., *Science,* 1986, 231, 1553; Schwander, et al., *J. Med. Virol.,* 1992, 36, 142; and Wieland, et al., *AIDS Res. Human Retrovir.,* 1991, 7, 861) suggesting that the protein is expressed and is immunogenic during natural infection (Volsky, et al., *Curr. Topics Micro. Immunol.,* 1995, 193, 157.

Due to vif's ability to activate viral replication in trans, an attenuated genetic vaccine design, similar to those utilized in the production of vaccines derived from toxic viral, bacterial, or parasitic components was employed in the present invention. The sequence variation and immunogenic potential present in vif genes derived from HIV-1 infected subjects was analyzed. Prototypic genetic variants were selected and the ability of those clones to induce humoral and cellular immune responses was studied in animals. The selected vif genetic variants were also functionally characterized through transcomplementation assays utilizing cells infected with a vif-defective HIV-1 clone. Attenuated, nonfunctional vif clones are demonstrated to induce immune responses capable of destroying native pathogen.

SUMMARY OF THE INVENTION

The present invention relates to a purified attenuated, non-functional vif protein.

The present invention relates to a vif protein comprising an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:23.

The present invention relates to an isolated nucleic acid molecule comprising a nucleotide sequence encoding an attenuated, non-functional vif protein.

The present invention relates to a nucleic acid molecule encoding a vif protein which comprises an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

The present invention relates to a nucleic acid molecule encoding a vif protein which comprises a nucleotide sequence selected from the group consisting of SEQ ID NO:27, SEQ ID NO:28, SEQ ID NO:29, SEQ ID NO:30, SEQ ID NO:31, SEQ ID NO:32, SEQ ID NO: 33, SEQ ID NO:34, SEQ ID NO:35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46.

The present invention relates to a pharmaceutical composition comprising the nucleic acid molecule encoding an attenuated, non-functional vif protein in a pharmaceutically acceptable carrier or diluent.

The present invention relates to a recombinant expression vector comprising a nucleic acid molecule comprising a nucleotide sequence encoding an attenuated, non-functional vif protein.

The present invention relates to a host cell comprising a recombinant expression vector comprising a nucleic acid molecule encoding an attenuated, non-functional vif protein The present invention relates to a purified antibody directed against an attenuated, non-functional vif protein.

The present invention relates to a method of immunizing a mammal against a virus comprising administering to cells of said mammal, a nucleic acid molecule that comprises a nucleotide sequence that encodes an attenuated, non-functional vif protein, wherein said nucleic acid molecule is expressed in said cells.

BRIEF DESCRIPTION OF THE FIGURES

FIG. 1 shows a comparison of the deduced amino acid sequences of vif derived from transmitter and non-transmitter mothers with well characterized HIV-1 molecular clones PNL43, SF-2, and Zr6. T-#, clones from transmitter subject; N-#, clones from non-transmitter subject; - - -, identity with the consensus sequence (Con; SEQ ID NO:1); . . . , represents gap; *, a stop codon.

FIGS. 3A and 3B show the results of an enzyme linked immunoabsorbent assay (ELISA) of anti-vif antibody responses in mice after immunization with a DNA construct expressing vif. Mouse sera was diluted in blocking buffer at a dilution of 1:500 and assayed as described herein. In FIG. 3A, mice were immunized with 50 µg of DNA. In FIG. 3B, mice were immunized with 100 µg of DNA per injection.

FIGS. 7A–7F show the amino acid sequences of preferred attenuated non-functional vif proteins of the present invention. FIG. 7A shows Vif-N13.pep (SEQ ID NO: 4); Vif-N15.pep (SEQ ID NO: 5); and Vif-N17.pep (SEQ ID NO: 6). FIG. 7B shows Vif-N22.pep (SEQ ID NO: 7); Vif-N24.pep (SEQ ID NO: 9); Vif-N26.pep (SEQ ID NO: 10): and Vif N27.pep (SEQ ID NO: 11). FIG. 7C shows Vif-N29.pep (SEQ ID NO: 12): Vif-N30 (SEQ ID NO: 13): Vif-T3.pep (SEQ ID NO:14); and Vif-T35.pep (SEQ ID NO: 16). Figure 7D shows Vif-T37.pep (SEQ ID NO: 17); Vif-T38.pep (SEQ ID NO: 18); and Vif-T39.pep (SEQ ID NO: 19). Figure 7E shows Vif-T4.pep (SEQ ID NO: 15); Vif-T40.pep (SEQ ID NO: 20): and Vif-T42.pep (SEQ ID NO: 21). FIG. 7F shows Vif-T43.pep (SEQ ID NO: 22) and Vif-T44.pep (SEQ ID NO: 23).

FIGS. 8A–8E show the nucleotide sequences of preferred attenuated, non-functional vif proteins of the present invention.

DETAILED DESCRIPTION OF THE INVENTION

Figure 2:
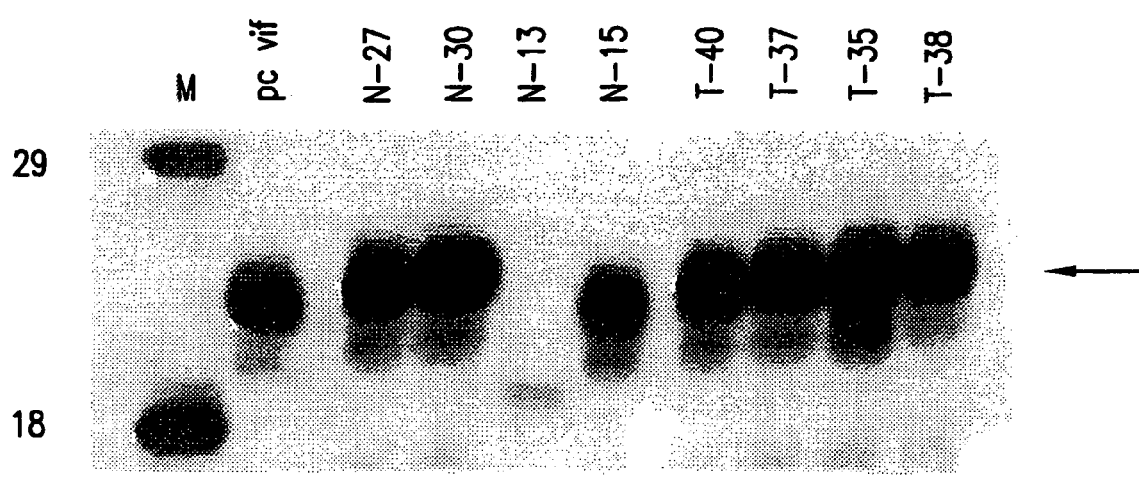
FIG. 2 shows a 10% SDS-PAGE of immunoprecipitates. Expression of HIV-1 vif clones derived from transmitter and non-transmitter mothers. Vif expression plasmids were used for coupled in vitro transcription/translation according to the manufacturer's instructions (Promega). Immunoprecipitation of the in vitro translated proteins was performed with vif antiserum as described herein. The designation of the vif clones is indicated on the top. The clone numbers designated with T- and N- are derived from the transmitter and non-transmitter mothers respectively. pCVif is the vif expression plasmid of HIV-1$_{SF2}$.

One of the major goals of AIDS research is the development of a vaccine against the HIV-1 virus. An effective vaccine should elicit strong humoral response along with an efficient and broad CTL response. This task is complicated because of the genetic heterogeneity of the HIV-1 virus. HIV-1 reverse transcriptase (RT) is prone to error and lacks the ability to proof-read, resulting in a mutation rate of 10$^{-4}$ per cycle per genome. Dougherty, et al., *J. Virol.*, 62, 2817. HIV-1 genome sequence variation has been observed in viruses isolated from different individuals as well as in virus isolated from a single person at different time points. Fisher, et al, *Nature,* 1988, 334, 444 and Meyerhans, et al., *Cell,* 1989, 58, 901. Based upon a large number of sequence analysis data, it is apparent that the structural genes env, gag and pol are the major target for mutations which lead to escape-variant viruses in patients by changing the neutralizing antibody and/or CTL epitopes. Pircher, et al., *Nature,* 1990, 346, 629; Reitz, et al., *Cell,* 1988, 54, 57; and Wolfs, et al., *Virol.,* 1991, 185, 195. Despite this, earlier experiments have indicated that structural and enzymatic genes of HIV-1 can be used successfully as nucleic acid-based vaccines in different animal models (Wang, et al., *Proc. Natl. Acad. Sci. USA,* 1993, 90, 4156; and Wang, et al., *AIDS,* 1995, 9 (Suppl A), S159) and prophylactic as well as therapeutic studies for DNA vaccines have commenced. The present invention is directed to development of vif, a HIV-1 accessory gene, as an immunogen cassette. When used in concert with other HIV-1 genes a broad immune response against all viral components may be induced, thus mimicking many aspects of the immune responses induced by a live attenuated vaccine.

In the present invention, induction of vif-specific humoral and cellular immune responses in mice have been observed to directly correlate with the concentration of DNA injected and number of boosts. Similar results were observed in T-cell proliferation and CTL assays, demonstrating that vif genes are immunogenic in vivo. Vif is known to present in both soluble and membrane associated form. Goncalves, et al., *J. Virol.*, 1994, 68, 704. Although anti-vif antibodies and vif-specific CTL responses have been shown in HIV-1 positive patients, epitopes involved in the presentation of vif to the immune system have not yet been defined. Lamhamedi-Cherradi, et al, *AIDS*, 1992, 6, 1249. How vif becomes exposed to the humoral immune system is unclear in these studies. The observed different immune response in the clones of the present invention suggest that the mutations in T-35, N-15 and pCVif may be associated with changes in antibody/CTL responses.

It is significant to note that some the point mutations present in all the T or N derived clones indicate that these mutations may be responsible for the difference in complementation and/or immune responses observed. Further mutational analysis of vif help resolve answer the regions involved in complementation. Proposed sites of vif activity include viral DNA synthesis, gp120 synthesis and transport, and gag processing. Borman, et al., *J. Virol.*, 1995, 69, 2058; Sakai, et al., *J. Virol.*, 1993, 67, 1663; and Von Schwedler, et al., *J. Virol.*, 1993, 67, 4945. Transcomplementation experiments with vif-defective HIV-1 provirus and wild-type HIV-1 vif-expressing cell lines indicate that vif acts at a late stage in virus replication/maturation and that vif transcomplementation occurs across HIV-1 strains. Blanc, et al., *Virol.*, 1993, 193, 186 and Hevey, et al., *Virus Res.*, 1994, 33, 269. Earlier experiments have shown that sera from the nontransmitter subject (N1) contains a high antibody titer against envelope protein and nonreplicating virus; whereas sera from the transmitter patient (TI) contains very low antibody titers against envelop proteins and highly replicating virus. Velpandi, et al., *DNA Cell Biol.*, 1996, 15, 571. These results correlate with the trans-complementation results observed in the present invention.

The present invention relates to isolated nucleic acid molecules comprising a nucleotide sequence encoding an attenuated, non-functional vif protein. As used herein, the term "attenuated, non-functional vif protein" is meant to refer to vif proteins that have no or reduced virion infectivity function compared to wild-type vif. In some embodiments of the invention, the nucleic acid molecules encode an attenuated, non-functional vif protein wherein the nucleotide sequence comprises deletions, additions, a point mutation(s), multiple substitutions, or introduction of a stop codon to render a shortened protein. In preferred embodiments of the invention, the isolated nucleic acid molecules of the invention encode a vif protein comprising the amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23. In other preferred embodiments of the invention, the isolated nucleic acid molecules encode a vif protein and comprise a nucleotide sequence selected from the group consisting of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46.

The nucleic acid molecules of the invention may be obtained from patients infected with the human immunodeficiency virus as described below in the Examples. Alternatively, the nucleic acid molecules of the invention may be prepared using the wild-type vif nucleotide sequence. The vif expression plasmid, pCVif, contains the vif gene from the well-characterized HIV-1 molecular clone, pHXB2, under the control of the cytomegalovirus (CMV) immediate early promoter, within the backbone plasmid, pRc/CMV (Invitrogen, San Diego, Calif.) as described in Nagashunmugam, et al., *DNA Cell Biol.*, 1996, 15, 353, incorporated herein by reference. This nucleic acid molecule may be used to prepare additional nucleic acid molecules encoding attenuated, non-functional vif proteins.

A number of methods can be used to design specific mutations in wild-type nucleic acid molecules to produce nucleic acid molecules encoding attenuated, non-functional vif proteins. For example, oligonucleotide-mediated mutagenesis is commonly used to add, delete, or substitute nucleotides in a segment of DNA whose sequence is known. Such methods are taught in, for example, Sambrook et al., *Molecular Cloning a Laboratory Manual*, Second Ed. Cold Spring Harbor Press (1989), pages 15.51 to 15.73, which is incorporated herein by reference. Briefly, the protocol for oligonucleotide-mediated mutagenesis involves the following steps: 1) cloning of an appropriate fragment of DNA, such as the vif nucleotide sequence from the pCVif expression plasmid, into a bacteriophage M13 vector; 2) preparation of single-stranded DNA from the recombinant bacteriophage M13; 3) design and synthesis of mutagenic oligonucleotides; 4) hybridization of the mutagenic oligonucleotides to the target DNA; 5) extension of the hybridized oligonucleotide by DNA polymerase; 6) transfection of susceptible bacteria; 7) screening of bacteriophage plaques for those carrying the desired mutation; 8) preparation of single-stranded DNA from the mutagenized recombinant bacteriophage; 9) confirmation by sequencing that the mutagenized bacteriophage M13 DNA carries the desired mutation and no other mutation; 10) recovery of the mutated fragment of DNA from the double-stranded replicative form of the recombinant bacteriophage M13; and 11) substitution of the mutagenized fragment for the corresponding segment of wild-type DNA in the desired expression vector.

Design and synthesis of the mutagenic oligonucleotides, which are tailored to the desired mutation in the nucleic acid molecule encoding vif, is described in detail in, for example, Sambrook et al., *Molecular Cloning a Laboratory Manual*, Second Ed. Cold Spring Harbor Press (1989), pages 15.54 to 15.56, which is incorporated herein by reference. For example, to substitute, add, or delete a single nucleotide into the wild-type vif nucleotide sequence, oligonucleotides of about 17–19 nucleotides in length which carry the mismatched nucleotide at the center or at one of the two nucleotide positions immediately 3' of the center are prepared. To substitute, add, or delete two or more contiguous nucleotides into the wild-type vif nucleotide sequence, oligonucleotides of about 25 or more nucleotides in length are prepared. These oligonucleotides comprise about 12 to 15 perfectly matched nucleotides on either side of the central looped-out region which contains the added or substituted nucleotides, or represents the portion of the wild-type DNA that is looped out. Using the strategy described above, one skilled in the art can prepare nucleic acid molecules having deletions, additions, substitutions, or premature stop codons, which encode attenuated, non-functional vif proteins. Oligonucleotide-mediated mutagenesis procedures are widely known to those skilled in the art.

Alternately, the nucleic acid molecules of the invention can be prepared using DNA synthesizers by standard DNA methodology. One skilled in the art readily understands that the genetic code is degenerate and, therefore, could prepare numerous DNA sequences encoding the same protein. In addition, one skilled in the art readily understands that amino acids can be substituted by other amino acids such that conservative substitutions are made. Accordingly, one skilled in the art can prepare nucleic acid molecules of the invention encoding attenuated, non-functional vif proteins.

Figure 1:
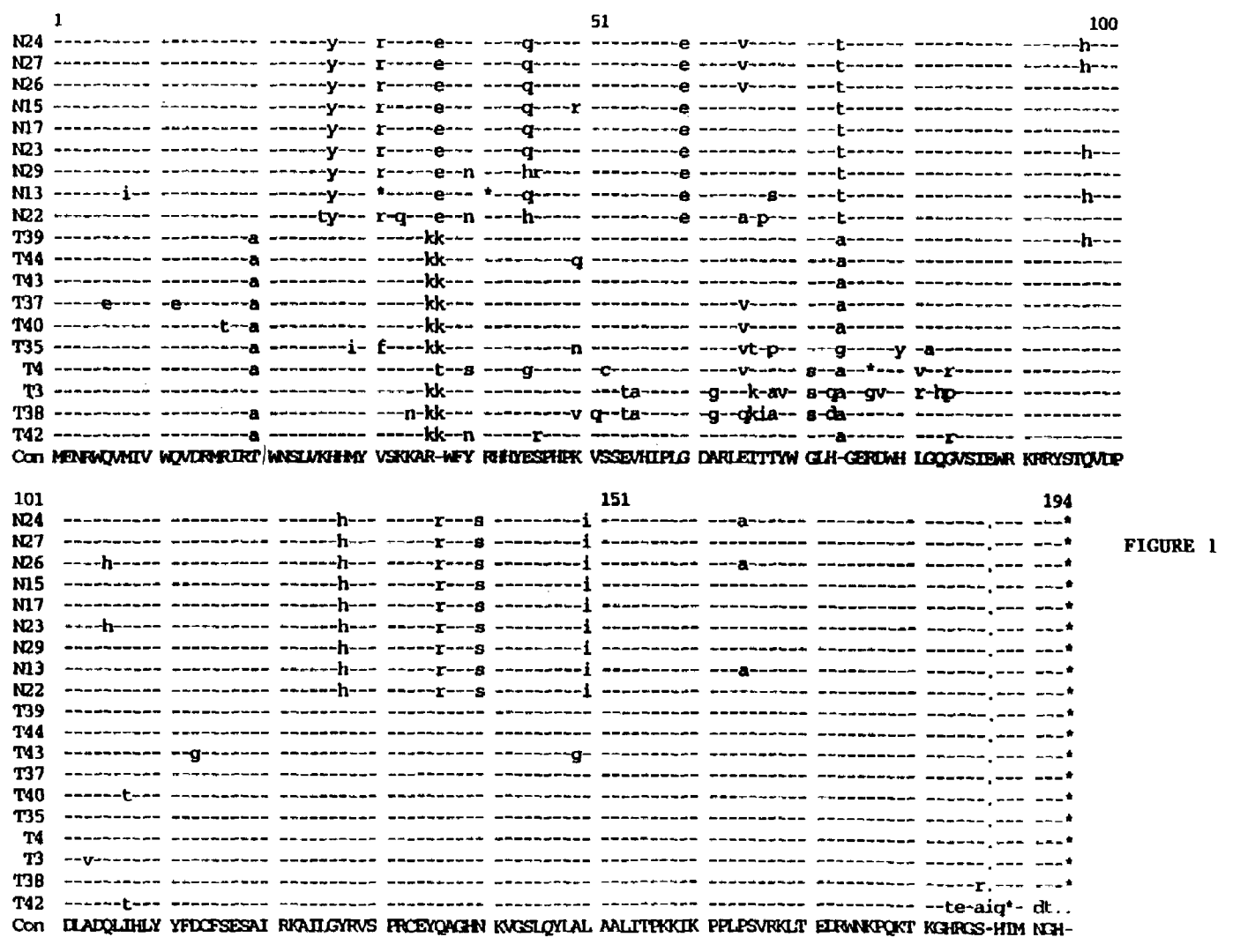

Preferred nucleic acid molecules of the invention encode attenuated, non-functional vif proteins having the amino acid (a.a.) and nucleotide sequences (nt.) (represented by particular SEQ ID Numbers) in Table 1. The specific amino acid sequences are shown in FIG. 1 and FIGS. 7A–7F. The specific nucleotide sequences are shown in FIGS. 8A–8E.

TABLE 1

| | SEQ ID NO: | | | SEQ ID NO: | |
|---|---|---|---|---|---|
| Vif Protein | a.a. | nt. | Vif Protein | a.a. | nt. |
| N13 | 4 | 27 | T3 | 14 | 37 |
| N15 | 5 | 28 | T4 | 15 | 38 |
| N17 | 6 | 29 | T35 | 16 | 39 |
| N22 | 7 | 30 | T37 | 17 | 40 |
| N23 | 8 | 31 | T38 | 18 | 41 |
| N24 | 9 | 32 | T39 | 19 | 42 |
| N26 | 10 | 33 | T40 | 20 | 43 |
| N27 | 11 | 34 | T42 | 21 | 44 |
| N29 | 12 | 35 | T43 | 22 | 45 |
| N30 | 13 | 36 | T44 | 23 | 46 |

The present invention also relates to vectors or recombinant expression vectors that comprise a nucleotide sequence that encodes an attenuated, non-functional vif protein. As used herein, the term "recombinant expression vector" is meant to refer to a plasmid, phage, viral particle or other vector which, when introduced into an appropriate host, contains the necessary genetic elements to direct expression of the coding sequence that encodes an attenuated, non-functional vif protein. In some embodiments of the invention, the vector or recombinant expression vector encodes an attenuated, non-functional vif protein wherein the nucleotide sequence comprises deletions, additions, point mutation(s), multiple substitutions, or introduction of a stop codon to render a shortened protein. In preferred embodiments of the invention, the vectors or recombinant expression vectors of the invention encode a vif protein comprising the amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:110, SEQ ID NO:111, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23. In other preferred embodiments of the invention, the vectors or recombinant expression vectors of the invention comprise a nucleic acid molecule encoding a vif protein which comprises a nucleotide sequence selected from the group consisting of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46.

One having ordinary skill in the art can isolate the nucleic acid molecule that encodes an attenuated, non-functional vif protein and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. The recombinant expression vectors of the invention are useful for transforming hosts which express an attenuated, non-functional vif protein.

The present invention also relates to a host cell that comprises the recombinant expression vector that includes a nucleotide sequence that encodes an attenuated, non-functional vif protein. In some embodiments of the invention, the host cell comprises the vector or recombinant expression vector that encodes an attenuated, non-functional vif protein wherein the nucleotide sequence comprises deletions, additions, point mutation(s), multiple substitutions, or introduction of a stop codon to render a shortened protein. In preferred embodiments of the invention, the host cells comprises vectors or recombinant expression vectors that encode a vif protein comprising the amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23. In other preferred embodiments of the invention, the host cell comprises vectors that comprise a nucleotide sequence selected from the group consisting of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46. Host cells for use in well known recombinant expression systems for production of proteins are well known and readily available.

The most commonly used prokaryotic system remains *E. coli*, although other systems such as *B. subtilis* and *Pseudomonas* are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion. Examples of prokaryotic host cells include bacteria cells such as *E. coli*, and yeast cells such as *S. cerevisiae*.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth. Commonly used eukaryotic systems include, but are not limited to, yeast, fungal cells, insect cells, mammalian cells, avian cells, and cells of higher plants. In preferred embodiments of the invention insect cells such as S. frugiperda, non-human mammalian tissue culture cells chinese hamster ovary (CHO) cells and human tissue culture cells such as HeLa cells are used as host cells. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of an attenuated, non-functional vif protein in E. coli. The commercially available plasmid pYES2 (Invitrogen, San Diego, Calif.) may, for example, be used for production in S. cerevisiae strains of yeast. The commercially available MAXBAC™ complete baculovirus expression system (Invitrogen, San Diego, Calif.) may, for example, be used for production in insect cells. The commercially available plasmid pcDNA1 or pcDNA3 (Invitrogen, San Diego, Calif.) may, for example, be used for production in mammalian cells such as Chinese Hamster Ovary cells. One having ordinary skill in the art can use these commercial expression vectors and systems or others to produce an attenuated, non-functional vif protein by routine techniques and readily available starting materials. See e.g., Sambrook et al., *Molecular Cloning a Laboratory Manual*, Second Ed. Cold Spring Harbor Press (1989), which is incorporated herein by reference.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

Examples of genetic constructs include the attenuated, non-functional vif protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes an attenuated, non-functional vif protein from readily available starting materials. Such gene constructs are useful for the production of an attenuated, non-functional vif protein.

Nucleic acid molecules that encode an attenuated, non-functional vif protein may be delivered to cells using any one of a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, transferrin-mediated transfection and other receptor-mediated means. The invention is intended to include such other forms of expression vectors and other suitable delivery means which serve equivalent functions and which become known in the art subsequently hereto.

In a preferred embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions.

In another preferred embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another preferred embodiment of the present invention, nucleic acid is delivered through folate receptor means. The nucleic acid sequence to be delivered to a host cell is linked to polylysine and the complex is delivered to the tumor cell by means of the folate receptor. U.S. Pat. No. 5,108,921 issued Apr. 28, 1992 to Low et al., which is incorporated herein by reference, describes such delivery components.

The present invention is also related to purified attenuated, non-functional vif proteins. The vif proteins of the invention have deletions, additions, point mutation(s), multiple substitutions, or introduction of stop codons to produce peptides that are attenuated and non-functional compared to wild type vif protein. In preferred embodiments of the invention, the attenuated, non-functional vif proteins of the invention comprise an amino acid sequence selected from the group consisting of SEQ ID NO:4, SEQ ID NO: 5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23. In other preferred embodiments of the invention, the attenuated, non-functional vif proteins of the invention consist of an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23. The vif proteins of the invention may be prepared by routine means using readily available starting materials as described above.

The particulars for the construction of expression systems suitable for desired hosts are known to those in the art and are described above. For recombinant production of the protein, the DNA encoding it is suitably ligated into the expression vector of choice and then used to transform the compatible host which is then cultured and maintained under conditions wherein expression of the foreign gene takes place. The proteins of the present invention thus produced are recovered from the culture, either by lysing the cells or from the culture medium as appropriate and known to those in the art. One having ordinary skill in the art can, using well known techniques, isolate an attenuated, non-functional vif protein that is produced using such expression systems. Methods of purifying an attenuated, non-functional vif protein from natural sources using antibodies which specifically bind to an attenuated, non-functional vif protein may be equally applied to purifying an attenuated, non-functional vif protein produced by recombinant DNA methodology.

In addition to producing these proteins by recombinant techniques, automated amino acid synthesizers may also be employed to produce vpr protein. It should be further noted that if the proteins herein are made synthetically, substitution by amino acids which are not encoded by the gene may also be made. Alternative residues include, for example, the ω amino acids of the formula $H_2N(CH_2)_nCOOH$ wherein n is 2–6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

Pharmaceutical compositions according to the invention comprise a pharmaceutically acceptable carrier in combination with either an attenuated, non-functional vif protein or a nucleic acid molecule of the invention encoding the same. In preferred embodiments of the invention, the pharmaceutical composition comprises a recombinant expression vector that encodes a vif protein comprising the amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

In other preferred embodiments of the invention, the pharmaceutical composition comprises a nucleic acid molecule encoding a vif protein which comprises a nucleotide sequence selected from the group consisting of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46. Pharmaceutical formulations are well known and pharmaceutical compositions comprising the compounds of the invention may be routinely formulated by one having ordinary skill in the art. Suitable pharmaceutical carriers are described in *Remington's Pharmaceutical Sciences*, A. Osol, a standard reference text in this field, which is incorporated herein by reference in its entirety.

The present invention also relates to an injectable pharmaceutical composition that comprises a pharmaceutically acceptable carrier and a compound of the present invention. The compound of the invention is preferably sterile and combined with a sterile pharmaceutical carrier. In some embodiments, for example, the compounds of the invention can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise a compound of the invention in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intrathecal or intraventricular administration may include sterile aqueous solutions which may also contain buffers, diluents and other suitable additives.

The pharmaceutical compositions of the present invention may be administered by any means that enables the active agent to reach the agent's site of action in the body of a mammal. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, pulmonary administration, e.g., by inhalation or insufflation, or intrathecal or intraventricular administration.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Formulation of therapeutic compositions and their subsequent administration is believed to be within the skill of those in the art.

According to the invention, the pharmaceutical composition comprising a nucleic acid molecule that encodes a vif protein of the invention may be administered directly into the individual or delivered ex vivo into removed cells of the individual which are reimplanted after administration. By either route, the genetic material is introduced into cells which are present in the body of the individual. Preferred routes of administration include intramuscular, intraperitoneal, intradermal and subcutaneous injection. Alternatively, the pharmaceutical composition may be introduced by various means into cells that are removed from the individual. Such means include, for example, transfection, electroporation and microprojectile bombardment. After the nucleic acid molecule is taken up by the cells, they are reimplanted into the individual.

The pharmaceutical compositions according to this aspect of the present invention comprise about 0.1 to about 1000 micrograms of DNA. In some preferred embodiments, the pharmaceutical compositions contain about 1 to about 500 micrograms of DNA. In some preferred embodiments, the pharmaceutical compositions contain about 25 to about 250 micrograms of DNA. Most preferably, the pharmaceutical compositions contain about 100 micrograms DNA.

The pharmaceutical compositions according to this aspect of the present invention are formulated according to the mode of administration to be used. One having ordinary skill in the art can readily formulate a nucleic acid molecule that encodes a vif protein of the invention. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline may be used. Stabilizers include gelatin and albumin.

DNA-based pharmaceutical agents are being developed as a new generation of vaccines. DNA therapeutics are typically plasmids that contain one or more DNA vaccines are typically plasmids which contain one or more genes from a particular pathogen or undesirable cell. Once injected, the coding sequence of the DNA vaccine is expressed in the patient or vaccinee as protein products and an immune response against the protein product is induced. Examples of protocols for delivering DNA which can be adapted for use with the present invention are described in U.S. Pat. No. 5,593,972 issued Jan. 14, 1997 to Weiner, U.S. Pat. No. 5,589,466 issued Dec. 14, 1996 to Felgner et al., U.S. Pat. No. 4,945,050 issued Jul. 31, 1990 to Sanford et al., U.S. Pat. No. 5,036,006 issued Jul. 30, 1991 to Sanford et al., PCT publication serial number WO 90/11092, PCT publication serial number WO 93/17706, PCT publication serial number WO 93/23552, and PCT publication serial number WO 94/16737 which are each incorporated herein by reference.

In preferred embodiments of the invention, pharmaceutical compositions comprising nucleic acid molecule comprising a nucleotide sequence encoding an attenuated, non-functional vif protein is administered to a mammal by the methods described above in order to induce a humoral and/or a cellular immune response to vif protein. In other embodiments of the invention, the pharmaceutical compositions of the invention can be co-administered with additional compounds. Such additional compounds include, for example, different viral proteins or nucleic acid molecules encoding a different viral proteins. The different viral proteins include, for example, gag, pol, env, vpr, vpu, and tat, and the like. Such elicited immune responses are protective against HIV or related animal viruses.

The present invention is also directed to antibodies directed against an attenuated, non-functional vif protein. As used herein, the term "antibody" is meant to refer to complete, intact antibodies, and Fab fragments and $F(ab)_2$ fragments thereof. Complete, intact antibodies include monoclonal antibodies such as murine monoclonal antibodies, chimeric antibodies and humanized antibodies. In some embodiments, the antibodies specifically bind to an epitope of vif or attenuated, non-functional vif. Antibodies that bind to an epitope are useful to isolate and purify that protein from both natural sources or recombinant expression systems using well known techniques such as affinity chromatography. Such antibodies are useful to detect the presence of such protein in a sample and to determine if cells are expressing the protein.

Hybridomas which produce antibodies that bind to vif protein, and the antibodies themselves, are useful in the isolation and purification of vif and attenuated, non-functional vif and protein complexes that include vif or attenuated, non-functional vif. In addition, antibodies may be specific inhibitors of vif activity. Antibodies which specifically bind to vif or attenuated, non-functional vif may be used to purify the protein from natural sources using well known techniques and readily available starting materials. Such antibodies may also be used to purify the protein from material present when producing the protein by recombinant DNA methodology.

The production of antibodies and the protein structures of complete, intact antibodies, Fab fragments and $F(ab)_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, vif or attenuated, non-functional vif, or an immunogenic fragment thereof, is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to vif or attenuated, non-functional vif, the hybridoma which produces them is cultured to produce a continuous supply of antibodies.

The present invention is further illustrated by the following examples, which are not intended to be limiting in any way. All references cited in the present application are incorporated in their entirety.

EXAMPLES

Example 1

Patients

Virus from one HIV-1 positive transmitter mother (T1) and one HIV-1 positive non-transmitter mother (N1) were used in the present invention. Peripheral blood lymphocytes (PBLs) obtained during the subject's third trimester were provided by the Mother Infant Cohort Study, Viral Epidemiology Branch, NCI (Rockville, Md.). A follow up examination was performed on the subjects and their offspring in order to determine transmission status.

Example 2

HIV-1 Isolation

Infected primary lymphocytes were co-cultivated with PHA-stimulated normal donor lymphocytes for 2 weeks. Virus production was monitored by: 1) measuring the levels of intracellular HIV-1 reverse transcriptase (RT) (Velpandi, et al., *J. Virol. Meth*., 1990, 29, 291; incorporated herein by reference) and 2) measuring the amount of HIV-1 p24 antigen released into the medium using a p24 antigen kit (Coulter Corporation), used according to the manufacturer's guidelines.

Example 3

DNA Preparation and PCR Amplification

High molecular weight (genomic) DNA was prepared from the infected PBLs and amplifies through PCR technology as described in Velpandi, et al., *J. Virol. Meth*., 1990, 29, 291, incorporated herein by reference. Briefly, the PCR mixture contained 5 to 10 µg of genomic DNA, 50 mM KCl, 2.5 mM $MgCl_2$, 10 mM Tris/HCl (pH 8.0), 800 µM dNTPs, 2.5 units Taq polymerase, 20 pmol oligonucleotide primers and double de-ionized water ($ddH_2O$) in a final volume of 100 µl. Reaction temperatures and cycling times were: 94° C.-denaturing (1 minute), 55° C.-annealing (1.5 minutes) and 72° C.-extension (2 minutes). The cycle was repeated 35 times. The primer sequences are as follows: Vif(+) 5'-GAAAGCTTATGGAAAACAGATGGCAG-3' (5046–5065) (SEQ ID NO:2); and Vif(−)5'-GCAAAGCTTTCATTGTATGGCTC-3' (5609–5626) (SEQ ID NO:3). The primers were tagged with a HindIII restriction site (in bold) for cloning purposes.

Example 4

Cloning and Sequencing

PCR-amplified product was used for cloning as described in Velpandi, et al., *DNA Cell Biol.*, 1996, 15, 571, incorporated herein by reference. Plasmid DNA positive for the vif gene was purified by mini preparations (Qiagen, Calif.) and quantitated by spectrophotometry in preparation for sequencing of the insert. Sequencing reactions were performed using an ABT automated sequencer and Dye Deoxy reactions (Applied Biosystems, Foster City, Calif.).

Example 5

Sequence Analysis

Sequence alignments were constructed using the Genetics Computer Group Sequence Analysis software package acquired through the Medical School Computer Facility of the University of Pennsylvania VAX system. Homology comparisons of amino acid sequences were carried out by sequence alignment programs.

Example 6

Construction of Vif-Defective Provirus

HIV-1 proviral DNA, pZr6, was used to construct a vif deletion mutant as described in Nagashunmugam, et al., *DNA Cell Biol.*, 1996, 15, 353, incorporated herein by reference. The resulting proviral clone, p911, contains an 80 amino acid deletion in the vif gene which does not affect the 3' reading frame. Briefly, HIV-1 proviral DNA pZr6 was derived from primary blood lymphocytes infected with $HIV_{Zr6}$ as described in Srinivasan, et al., *Gene*, 1987, 52, 71–82, incorporated herein by reference in its entirety. A deletion was introduced into pZr6 to prepare p911. The mutant was constructed so as not to interfere with the upstream pol gene or the downstream vpr gene. Plasmid pZr6 contains two NdeI sites in the vif gene at nucleotide positions 476 and 716. Srinivasan, et al. *Gene*, 1987, 52, 71–82. The NdeI fragment (477–716) was deleted from pZr6 and the ends were religated to construct p911, an in-frame mutant that has 80 amino acids deleted in the central region of the vif protein.

Example 7

Construction of Vif Expression Vectors

The vif expression plasmid, pCVif, contains the vif gene from the well-characterized HIV-1 molecular clone, pHXB2, under the control of the cytomegalovirus (CMV) immediate early promoter, within the backbone plasmid, pRc/CMV (Invitrogen, San Diego, Calif.) as described in Nagashunmugam, et al., *DNA Cell Biol.*, 1996, 15, 353, incorporated herein by reference. The vif genes from the maternal samples were cloned into the Invitrogen expression vector, pCDNA3, under the control of the CMV promoter. The vif reading frames were verified through sequence analysis using the forward primer, T7, and the reverse primer, SP6. Briefly, to construct a vif expression vector (pCVif), an Eco R1—Eco R1 1.1 kb fragment from pHxB2 (map coordinates 4,647–5,742, Ratner, et al., *Nature*, 1985, 313, 277–284, incorporated herein by reference in its entirety) was cloned under the control of the cytomegalovirus immediate early promoter into plasmid pCDNA3 obtained from Invitrogen. This fragment also contains flanking sequences from parts of the pol and vpr genes, which are not transcriptionally active as shown in a similar construct by Blanc, et al. (*Virology*, 1993, 193, 186–192).

Example 8 in Vitro Translation of Vif

In vitro transcription and translation was performed on 1 µg of vif expression construct DNA using T7 RNA polymerase according to the manufacturer's instructions (Promega, Madison, Wis.). Five (5) µl of the in vitro translation reaction products were combined with 500 µl of radioimmunoprecipitation assay buffer and immunoprecipitated with rabbit anti-vif antiserum as described. Mahalingam, et al., *Virol.*, 1995, 214, 647.

Example 9

Cells

Rhabdomyosarcoma (RD) cells, obtained from the American Type Culture Collection (ATCC), were grown in a monolayer at 37° C. in 5% $CO_2$ in Dulbecco's modified Eagle's medium supplemented with 10% fetal bovine serum, 1% penicillin, 1% streptomycin and 1% L-glutamine. Lymphocytoid cell lines obtained from ATCC were maintained as suspension cultures in RPMI 1640 medium, supplemented with 10% fetal bovine serum, penicillin (100 U/ml) and L-glutamine (540 µg/ml) at 37° C. with 5% $CO_2$. Phytohemagglutinin-stimulated (10 µg/ml) PBLs were maintained in RPMI 1640 medium containing 10% T-cell growth factor.

Example 10

Immunization of Mice with Vif Constructs

For immunization experiments in mice, 3 different vif constructs were used. The vif clones selected were T-35 (from transmitter), N-15 (from non-transmitter) and pCVif (vif gene of HIV-1$_{SF-2}$). pCDNA3 vector DNA was used as a negative control. In order to enhance DNA uptake, the quadriceps muscles of BALB/c mice were injected with 100 µl of 0.25% bupivacaine 48 hours before DNA injection. Fifty (50) or 100 µg of each vif expression plasmid was injected in a final volume of 100 µl into each of 4 mice. The animals were boosted 3 times at two week intervals.

Example 11

ELISA Binding of Mouse Serum to rvif Protein

ELISA was performed on mouse serum as described in Wang, et al., *AIDS,* 1995, 9 (Suppl A), S159. Briefly, ELISA plates were coated with recombinant vif (rvif) protein at concentration of 100 ng/well for the binding assays. Mouse sera were diluted (1:100 and 1:500) in blocking buffer, tagged with anti-mouse IgG conjugated to horseradish peroxidase (HRP) and detected by TMBlue substrate. The non-specific binding and the prebled sera binding were subtracted from the specific binding of the DNA injected animal sera.

Example 12

CTL Assay using Vaccinia Expressing vif

DNA injected mice were sacrified 7 weeks after the first immunization, and their spleens were removed for CTL and T-cell proliferation assays as described in Wang, et al., *DNA Cell Biol.*, 1993, 12, 799. Briefly, P815 cells infected with vif-expressing vaccinia (VV:gag kindly provided by NIH AIDS Reagent and Reference Program) were used as target cells. Ten (10) µCi of $Na_2CrO_4$ ($^{51}Cr$, 534 mCi/mg, Dupont Co.) was added to $1\times10^6$/ml target cells which were subsequently incubated for 2 hours at room temperature. The cells were then washed 3 times with serum-free media and diluted to a volume of $1\times10^5$ cells/ml in RPMI 1640/10% calf serum. The effector spleen cells were washed once, resuspended and diluted to a concentration of $1\times10^7$ cells/ml of RPMI medium. 1:2 serial dilutions were made from this stock cell solution ($5\times10^6$, $2.5\times10^6$ and $1.25\times10^6$ cells/ml). One hundred (100) µl of these effector cell solutions were aliquoted into a 96-well microliter flat bottom plate. One hundred (100) µl of target cell solution was added to each well. The resultant effector to target cell ratios were 100:1, 50:1, 25:1 and 12.5:1. In order to determine the spontaneous or maximum chromium release, respectively, target cells were mixed with either 100 µl of media alone or 1% Triton-X. The effector and target cells were then incubated at 37° C. in a 5% $CO_2$ incubator for 5 hours. A 100 µl aliquot of supernatant was removed from each well, and the amount of $^{51}Cr$ release was measured in a gamma counter. The formula for calculation of the specific CTL release is below: 100×[(experimental release-spontaneous release)/maximum release-spontaneous release)]. Note: maximum release was determined by lysis of target cells in 1% Triton X-100.

Example 13

CTL Assay using Clinical HIV-1 Isolates

HeLa CD4+ cells expressing, mouse MHC-I were infected with HIV-1 clinical isolates and used as target cells in the CTL assay. The CTL assay was performed as described in Chada, et al., *J. Virol.*, 1993, 67, 3409.

Example 14

T Cell Proliferation Assay

Assays were performed in triplicate. Splenocytes were isolated as discussed above, resuspended in RPMI 1640 and diluted to a concentration of $3.3\times10^6$ cells/ml. A 150 µl aliquot was immediately added to each well of a 96-well microtiter flat bottom plate. Fifty (50) µof protein or peptide was added to each well to final concentrations of 10.0, 1.0 or 0.1 mg/ml. The cells were incubated at 37° C. in a 5% $CO_2$ incubator for 3 days. One (1) µCi of tritiated thymidine was added to each well, and the cells were incubated overnight under the same conditions. The cells were harvested using automated cell harvester (Tomtec, Orange, Conn.) and the amount of incorporated tritiated thymidine was measured in a beta counter. In order to ensure that the cells were healthy, 5 mg/ml of PHA was used as a non-specific stimulator in a positive control sample.

Example 15

Transcomplementation of vif Defective Proviral DNA with vif Genes from Maternal Samples RD cells ($1\times10^6$) were co-transfected with 10 µg of a vif defective proviral clone, p911, and 10 µg pCVif or vif expression plasmid from transmitter or non-transmitter subjects using lipofectin from Boehringer Mannheim (Indianapolis, Ind.). The co-transfected cells were washed after an 8 hour incubation and resuspended in DMEM media. Culture supernatant was collected after a 72 hour incubation, centrifuged to remove cell debris, passed through a 0.45 µm filter, and assayed for p24 production (Coulter Corporation). PBMCs ($1\times10^7$) were infected with an amount of virus equivalent to 100 ng of p24 antigen. Virus-inoculated cells were incubated for 4–6 hours at 37° C. and 5% $CO_2$, washed 3 times with PBS and resuspended in 10 ml of fresh RPMI 1640. An aliquot of the culture supernatant was collected every 3 days in order to quantitate virus production by measuring the amount of p24 antigen released into the medium.

Example 16

Characterization of Viruses Isolated from Patients

The HIV-1 positive transmitter and non-transmitter mothers included in the present invention were selected from an AIDS cohort study. The mother and the non-transmitter mother are referred to as T1 and N1, respectively. The clinical status of the subjects and the replication kinetics of their viral isolates are presented in Table 2. Uncultured lymphocytes from each subject were used in order to obtain wild-type sequences unmodified by in vitro selection conditions. In PBMC co-cultivation assays, T1 viral samples replicated very well in normal donor PBLs; whereas N1 viral samples did not replicate in either primary lymphocytes or macrophages.

TABLE 2

| Subject | Clinical Stage | PCR | Virus Coculture in PBMC | Infection in CD4+ Cell Lines |
|---|---|---|---|---|
| Transmitter | Asymptomatic | +++ | +++ | +++ |
| Non-Transmitter | Asymptomatic | ++ | — | — |

Example 17

Sequence Variation of Vif Gene in Vivo

In order to investigate the genetic variability of the vif gene in these subjects, ten clones from each subject were sequenced and computer-aligned by degree of homology. The nucleotide sequences were then translated into protein sequences. Deduced amino acid sequences were used in the final comparison, since not all nucleotide sequence chances resulted in amino acid sequence changes. The aligned amino acid sequences from these patients are shown in FIG. 1. Clone numbers with the designations, 'T' and 'N' represent variants isolated from transmitter and non-transmitter mothers, respectively. Sequence alignment revealed that each subject had a unique and highly conserved set of sequences within their virus pool. Most of the nucleotide changes were point mutations which generally resulted in substitutions, versus duplications or insertions, within the protein sequence. Three clones encoded attenuated proteins. Clone T-42 had a 5 amino acid deletion at its 3' end due to a premature stop codon. Clone N-13 had two stop codons (positions 31 and 41) and clone T-4 had a single stop codon (position 77), each of which was introduced within a set of three nucleotides, keeping the reading frame intact 3' to the mutation. The fact that the majority (17 of 20) of the clones encode full-length sequences suggests that there are few defective vif genes present within these patients' viral pools. It is interesting to note that most of the vif point mutations are present in the 5' portion of the gene rather than in the 3' region. Significant differences were found between clones at positions 20, 27, 31, 36, 37, 45, 60, 74, 127, 136, 140 and 150.

In order to determine the nature and the sequence variation of vif gene in vivo, we cloned and analyzed vif variants present in uncultured PBMCs from HIV-1 positive subjects. Analysis of 20 different vif sequences from two subjects (10 from each subject) revealed that vif is highly conserved (approximately 90%) within a particular patient at a given time point. Although, Wieland, et al. (Virol., 1994, 203, 43) reported that the 3' portion of the vif gene is highly variable, the results of the present invention indicate that the 5' portion (aa 20–85) is more variable and the 3' portion is well-conserved. In support of the results herein, previous mutagenesis experiments have shown that the C terminus of vif (aa 171 to 192) is essential for stable association of vif with membranes. Goncalves, et al., J. Virol., 1994, 68, 704. Among the 20 sequences we analyzed, only two clones had premature stop codons indicating that 90% of vif genes isolated were intact in vivo. This result, along with previously published data, suggests that a complete vif gene is essential for viral replication in vivo. Gabudza, et al., J. Virol., 1992, 66, 6489; and Sova, et al., J. Virol., 1995, 69, 2557.

The 20 deduced vif protein sequences from these clones exhibited 75% conservation (25% variation) over the entire (192 aa) length. In particular, two antigenic domains, aa 87–94 (IEWRKKRY) (SEQ ID NO: 24) and aa 172–178 (DRWNKPQ) (SEQ ID NO: 25), recognized by HIV-1 positive sera (Wieland, et al., AIDS Res. Human Retrovir., 1991, 7, 861) are well conserved in all 20 clones. The well-conserved nature of these two regions may be responsible for the cross antigenic properties exhibited by these clones. In addition, a sequence which is conserved in 34/38 lentivirus vif, SLQYLA (144–149)(SEQ ID NO: 26) (Oberste, et al., Virus Genes, 1992, 6, 95), is also conserved in each of the 20 vif clones sequenced in the present invention. In previous studies, computer alignment analyses has shown that amino acids 21 to 30, 103 to 115 and 142 to 150 of vif are highly conserved among HIV-1, HV-2 and SIV. Myers, et al., Human Retrovir. AIDS, 1988. Clones analyzed in the present invention, however, were generally conserved sequences within aa 103–115 and aa 142–150, but not within aa 21–30. Vif protein has been characterized as a cysteine protease with Cys 114 marking its active site and His 48 considered to be important for activity. Guy, et al., J. Virol., 1991, 65, 1325. In the sequences of the present invention, Cys 114, as well as Cys 133 (the only other cystine in vif) and His 48, were well conserved.

Phylogenetic tree analysis (data not shown) found 3 major families within the 20 patient clones. Ninety (90%) percent of N-derived clones formed a family and 80% of T-derived clones formed a family while the remaining clones, N-30, T-3 and T-38, exhibited greater diversity and formed a Separate group (data not shown). When distance comparison was performed, intrapatient variation between the transmitter clones was 12%, versus a variation of 10% between non-transmitter clones. The similarity between the subjects' variant clones and the established laboratory molecular clones, $HIV_{SF-2}$, $HIV_{NL43}$ and $HIV_{Zr6}$, was also evaluated. The subject isolates shared a higher degree of homology with other clones within their transmitter status group than with any of the laboratory-maintained viral isolates. Based upon their sequence variation, 4 clones from each patient were selected for preliminary translation/immunization experiments (see below).

Phylogenetic tree analysis also illustrated that, in spite of intra-patient variation, clones from the transmitter and non-transmitter subjects clustered separately. In vitro transcription/translation of 8 constructs (four from each subject) resulted in the expression of a 23 KDa protein, except in the case of clone N-13 which has a premature stop codon. This suggests that the various mutations present in these vif constructs did not affect the expression kinetics and stability of the protein.

Example 18

Expression of Vif Clones

In vitro transcription/translation was performed upon 5 clones from each group in order to assess their levels of vif expression. Results are presented in FIG. 2. The products from the in vitro translation reactions were immunoprecipitated with vif antiserum and subjected to gel electrophoresis. pCVif (full length vif from HIV-1 strain SF2) and p911 (vif mutant) provirus were used as a positive and negative control, respectively. In vitro translation with pCVif and each of the full length vif expression plasmids produced a 23 kDa protein; whereas clones p911 and N-13 did not result a protein product of 23 kDa size, probably due to the presence of premature stop codons. Two (2) clones from each subject group were selected for further evaluation, based upon similar serological characteristics (data not shown). The patient clones selected as representatives from each croup were T-35 (from transmitter) and N-15 (from non-transmitter). Each of these clones contain mutations characteristic of their particular group and represent the highest level of diversity within these groups. It is interesting to note that mutations within clone N-15 are dispersed throughout the full length gene; whereas mutations within clone T-35 are clustered at the 5' end of the gene.

Example 19

Induction of Humoral Responses in Vivo

Specific anti-vif immune responses were apparent in sera collected from mice immunized with T-35, N-15 and pCVif expression plasmids, but not in sera from mice immunized by pcDNA3 vector alone. The induction of immune response correlated with DNA injection concentration, as well as the number and time interval between boosts. Sera from 4 mice injected with either 50 or 100 μg of vifDNA had specific reactivity to vif protein when measured by ELISA (FIG. 3). Induction of the humoral response was dose-and time-dependent. Injection of 50 μg of DNA induced an immune response detectable by ELISA at 15 days following the first injection. This response increased after subsequent boosts, reaching a maximum level 45 days after 2 boosts (Panel A). Injection with 100 μg of DNA induced a response that reached a maximum level only 28 days after a single boost (Panel B). In addition, the antibody response can be elevated 219 days after the three injections with a single boost of DNA (data not shown). The level of antibody response varied between vif clones. Most importantly, the non-transmitter clone, N-15, induced a higher serological response than the transmitter clone, T-38, or pCVif. This suggests that non-transmitter vif is capable of inducing a more efficient B-T helper dependent response than transmitter vif in this strain of mice.

Example 20

Induction of Cellular Responses in Vivo using Vaccinia Expressing Vif

Figure 4:
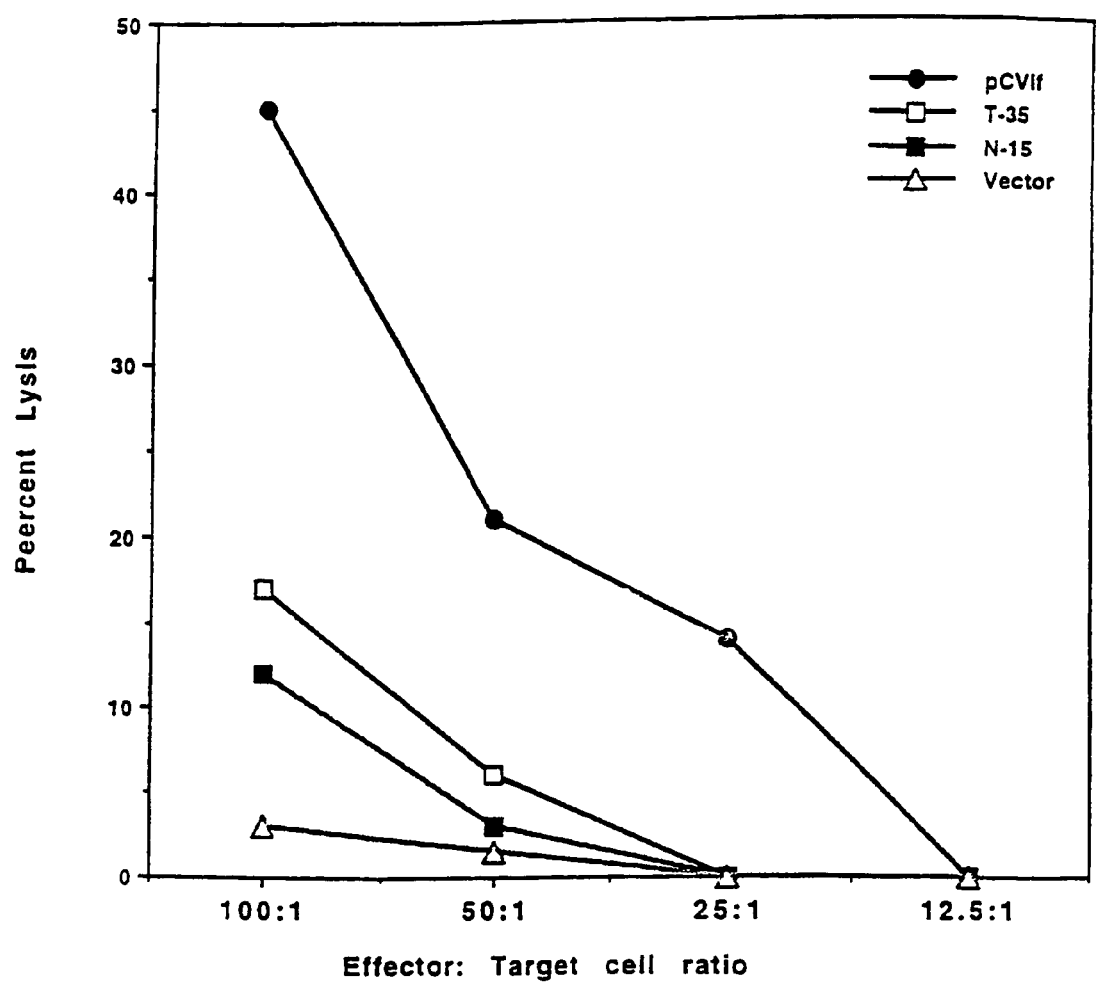
FIG. 4 shows the results of a chromium release assay whereby lysis of murine targets (p815) expressing vif protein by splenocytes from mice immunizied with vif expression constructs. p815 cells (1×10$^5$/ml) were infected with vaccinia expressing vif (VV:gag) and incubated for 16 hours to express the Vif protein. The target cells were labeled with $^{51}$Cr for 1–2 hours and used to incubate the stimulated splenocytes for 6 hours. Specific lysis (%) was calculated according to the formula described herein.
Figure 5A:
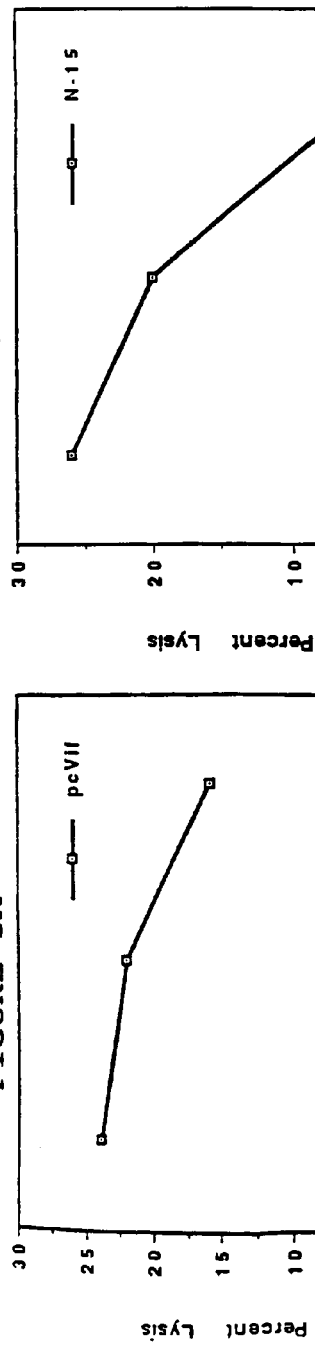
FIGS. 5A, 5B, 5C and 5D show the results of a chromium release assay whereby lysis of HeLa CD4+/D$^d$ cells infected with clinical HIV-1 isolate by splenocytes from mice immunized with vif expression cassette. HeLa CD4+/D$^d$ cells (10$^6$) were infected with cell-free HIV-1 clinical isolate followed by a week incubation to allow the cells to infect and express viral proteins. One week postinfection, the target cells were labeled with $^{51}$Cr for 1–2 hours and used to incubate the stimulated splenocytes for 6 hours. Specific lysis (%) was calculated according to the formula described herein.
Figure 5B:
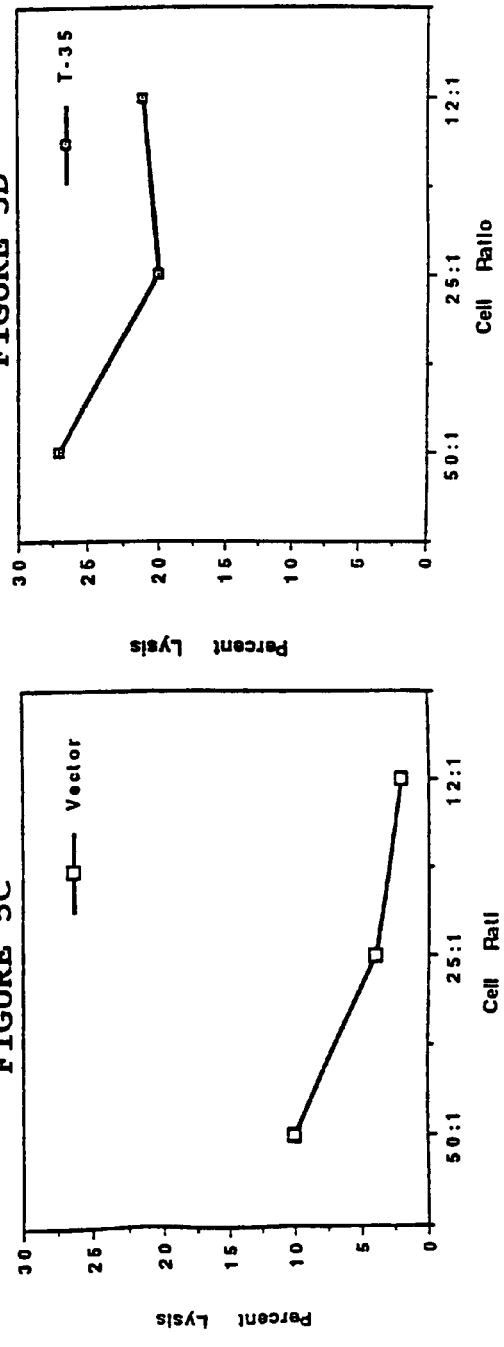
Figure 5C:
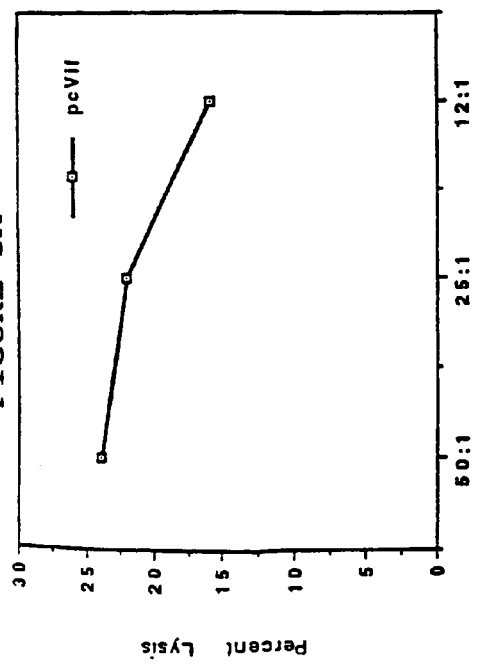
Figure 5D:
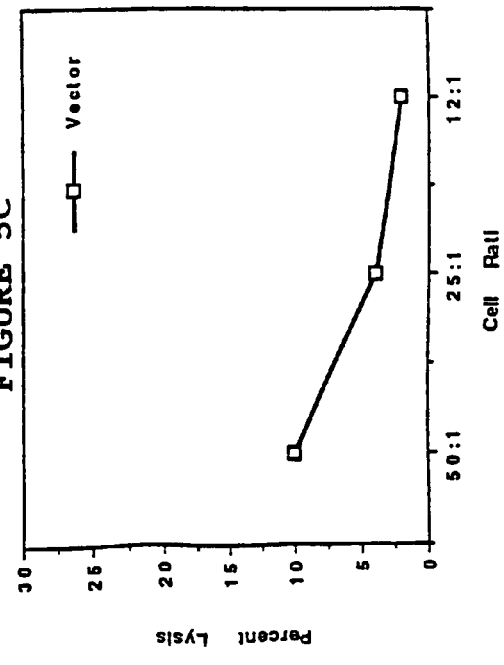

Four mice, each immunized with one of the vif constructs, were given an additional boost 15 days after first injection. Two mice were subsequently sacrificed and their splenocytes were used in a cytotoxic T cell (CTL) assay. p815 cells infected with vif-expressing vaccinia were used as target cells. Non-specific lysis by splenocytes from vif DNA immunized and naive mice was measured using p815 cells infected with non-vif-expressing vaccinia as target cells. Specific target lysis is presented in FIG. 4. The level of specific CTL activity varied between the vif constructs. Splenocytes from mice immunized with clone pCVif exhibited 45% lysis at a effector: target ratio of 100:1. Clones T-35 and N-15 exhibited 17 and 12% lysis, respectively, at the same ratio. These results clearly demonstrate that vif DNA immunization induces specific CTL responses. The differences in the levels of CTL activity induced by vif gene inoculation between the various patient clones may be due to mutations within the CTL epitopes expressed by vaccine targets or differences in immune responsiveness in this haplotype.

Example 21

Evaluation of Cellular Responses in Vivo using Human Targets Infected with a Clinical HIV-1 Isolate In order to evaluate the ability of the vif clones to induce lysis of virally infected targets, we used HIV-1 infectable HeLa CD4/$D^d$ cells which express both the CD4 receptor and the murine class I H-$2D^d$ restriction element, as targets in the CTL assay. These cells were infected with an HIV-1 isolate derived from a symptomatic AIDS patient for 7 days. FIG. 5 (A–D) represents CTL assay results. Splenocytes obtained from mice injected with each of the DNA constructs exhibited vif-specific lysis. Clones T-35, N-15 and pCVif presented with 27, 26 and 24% lysis, respectively, at an effector:target ratio of 50:1. All three clones exhibited 20% lysis at a ratio of 25:1. This demonstrates that a cellular immune response against native HIV-1 isolates can be generated through genetic vaccination with vif expression vectors.

Example 22

Induction of Antigen Specific T-Cell Proliferation

Figure 6:
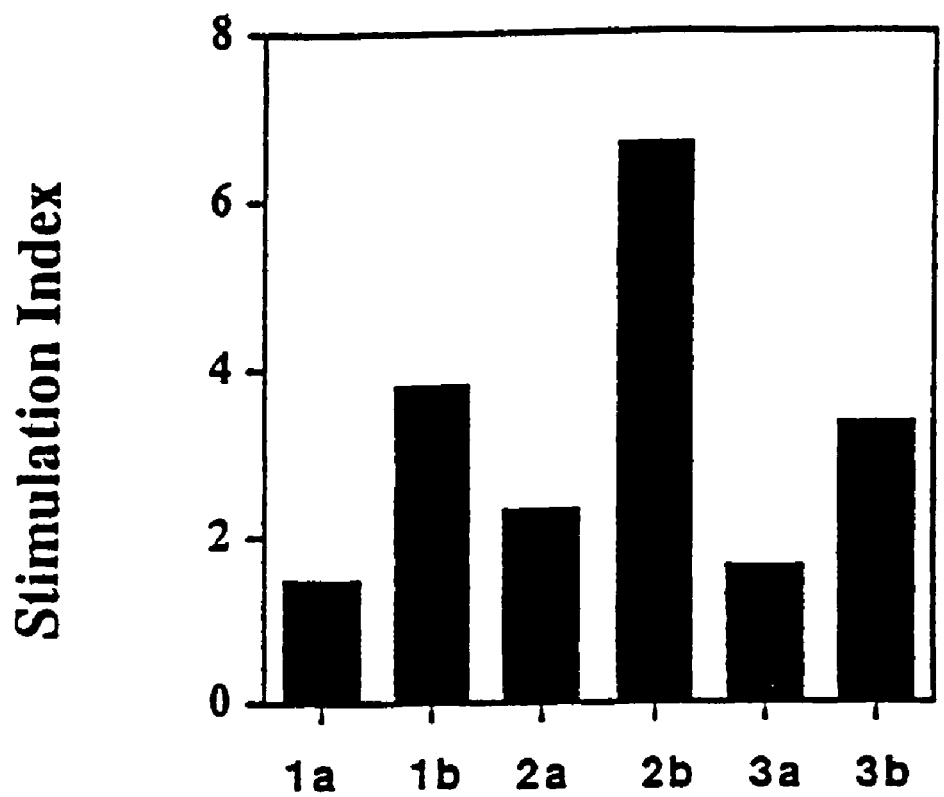
FIG. 6 shows the results of a proliferation assay showing activation and T cell proliferative response to recombinant Vif. Recombinant Vif (10 µg/ml) was plated in each well to stimulate proliferation of T cells. Lectin PHA (10 µg/ml) was used as a polyclonal stimulator positive control. Stimulation index was calculated as the level of radioactivity detected from the cells stimulated with specific protein divided by the level detected from the cells in media. Lanes 1a and 1b are from mice immunized with 50 and 100 µg of pCVif, Lanes 2a and 2b are from mice immunized with 50 and 100 µg of clone T-35; Lanes 2a and 2b are from mice immunized with 50 and 100 µg of clone N-15.

Specific T-cell proliferation responses against HIV-1 vif protein were also studied in DNA-immunized animals. Lymphocytes from vif-immunized mice demonstrated a significant proliferative response against rvif protein. FIG. 6 illustrates the proliferation index of different vif constructs versus DNA injection concentrations. The results show that the MHC class II-dependent $T_h$ (helper) cell response is dose dependent. For each construct, the stimulation index is almost 2-fold higher in mice injected with 100 μg of vif DNA than in mice injected with 50 μg of vif DNA. Comparison of the three different vif constructs also indicates that, at each injection concentration, clone T-35 induces a higher stimulation index than either N-15 or pCVif.

Example 23

Transcomplementation of HIV-1 Vif-Provirus with Vif Expression Plasmids

As expected, transient transfection of RD cells with HIV-1 (vif-) proviral DNA and vif expression plasmids did not reveal any differences in virus production between T-derived, N-derived or control plasmids (data not shown). Any differences in vif function would be demonstrated at the level of new infection. When rescued virus was used to infect primary lymphocytes, however, a significant difference was observed in virus pathogenesis between T- and N-derived and control plasmids (Table 3). The vif-negative proviral clone (p911) alone was unable to infect primary PBLs as cell-free virus. When trans-complemented virus (p911+pCVif) was used to infect the PBLs, infectivity was five-fold less than that of wild-type virus. In contrast, each of the T-derived clones tested were able to rescue the (vif–) mutant (approximately 100% positive virus control). However, none of the N-derived clones were able to efficiently infect PBLs as cell-free virus. Therefore, N-15 and similar N-derived clones were able to induce anti-HIV immune responses in mice in the absence of functionality.

TABLE 3

| Samples | DNA Used to Derive Viruses for Infection | Amount of p24 Released (ng/ml) |
|---|---|---|
| Proviral Clone | pZr6 | 101,846 |
| Vif Mutant | p911 | 60 |
| Vif Mutant + pCVif | p911 + pCVif | 22,679 |
| Vif Mutant + Transmitter | p911 + T1-40 | 21,896 |
| Clones | p911 + T1-37 | 17,230 |
| | p911 + T1-35 | 19,470 |
| | p911 + T1-38 | 81,570 |
| Vif Mutant + Non- | p911 + N1-13 | 520 |
| Transmitter Clones | p911 + N1-15 | 530 |
| | p911 + N1-17 | 1,090 |
| | p911 + N1-27 | 1,277 |
| | p911 + N1-30 | 715 |

RD cells were transfected with 10 μg of pZr6, vif mutant p911, p911 and vif expression plasmids from different patient samples. Virus pools were prepared from supernatant collected 72 hours after transfection. Virus equivalent to 100 ng of p24 antigen was subsequently used to infect $10\times10^6$ PBMCs. Infection was monitored by p24 antigen production.

Example 24

Observations

N-derived clones were attenuated in their ability to transcomplement vif defective HIV-1 provirus. One of the clones analyzed, N-15, was also immunologically functional and capable of generating an immune response against wild-type HIV-1 virus. A non-functional yet immunogenic clone, such as N-15 in the present invention, could be an effective component of a genetic vaccine directed against HIV-1. It has been shown in the present invention that vif alone can generate an effective response against native HIV-1 virus in vitro. Such immunogens could be useful in a therapeutic setting to target the immune response against native vif expressing viruses. While it is likely that escape variants can occur viruses expressing defective vifs due to this selection might now exhibit attenuated in vivo growth kinetics. In a similar manner a prophylactic vaccine which includes vif could serve to both limit viral escape and contribute to lowering the viral set point during the early infection events.

---

What is claimed is:

1. An isolated nucleic acid molecule comprising a nucleic acid sequence encoding an attenuated non-functional vif protein, wherein said nucleotide sequence encodes an Alanine in place of Proline at position 162 of SEQ NO:1.

2. A pharmaceutical composition comprising a nucleic acid molecule of claim 1 in a pharmaceutically acceptable carrier or diluent.

3. A recombinant expression vector comprising a nucleic acid molecule of claim 1.

4. A host cell comprising a recombinant expression vector comprising a nucleic acid molecule of claim 1.

5. A plasmid comprising a nucleotide sequence encoding an isolated, attenuated non-functional vif protein, wherein said nucleotide sequence encodes an Alanine in place of Proline at position 162 of SBQ ID NO: 1.

6. A nucleic acid molecule comprising a nucleotide sequence encoding an attenuated, non-functional vif protein, wherein said nucleic acid molecule comprises a nucleotide sequence which encodes an amino acid sequence selected from the group consisting of SEQ ID NO:4, SEQ ID NO:9, and SEQ ID NO:10.

7. The nucleic acid molecule of claim 6 wherein said nucleic acid molecule comprises a nucleotide sequence which encodes the amino acid sequence of SEQ ID NO: 4.

8. A recombinant expression vector comprising a nucleic acid molecule of claim 6.

9. A host cell comprising a nucleic acid molecule of claim 6.

10. A nucleic acid molecule comprising a nucleotide sequence encoding an attenuated, non-functional vif protein, wherein said nucleic acid molecule comprises a nucleotide sequence selected from the group consisting of SEQ ID NO:27, SEQ ID NO:32, and SEQ ID NO:33.

11. The nucleic acid molecule of claim 10 wherein said nucleic acid molecule comprises the nucleotide sequence of SEQ ID NO: 27.

12. The recombinant expression vector of claim 8 wherein said nucleic acid molecule comprises a nucleotide sequence which encodes the amino acid sequence of SEQ ID NO: 4.

13. A host cell comprising a nucleic acid molecule of claim 10.

14. The host cell of claim 13 wherein said nucleic acid molecule comprises SEQ ID NO:27.

15. A recombinant expression vector comprising a nucleic acid molecule of claim 10.

16. The recombinant expression vector of claim 15 wherein said nucleic acid molecule comprises SEQ ID NO:27.

17. The host cell of claim 9 wherein said nucleic acid molecule comprises a nucleotide sequence which encodes the amino acid sequence of SEQ ID NO: 4.

18. A plasmid comprising a nucleotide sequence encoding an isolated, attenuated, non-functional vif protein, wherein said protein comprises an amino acid sequence selected from the group consisting of SEQ ID NO:4, SEQ ID NO:9, and SEQ ID NO:10.

19. The plasmid of claim 18 wherein said protein comprises the amino acid sequence of SEQ ID NO: 4.

20. A plasmid comprising a nucleotide sequence encoding an isolated, attenuated, non-functional vif protein, wherein said nucleotide sequence is selected from the group consisting of SEQ ID NO:27, SEQ ID NO:32, and SEQ ID NO:33.

21. The plasmid of claim 20 wherein said nucleotide sequence is SEQ ID NO:27.

* * * * *

SEQUENCE LISTING

<160> NUMBER OF SEQ ID NOS: 46

<210> SEQ ID NO 1
<211> LENGTH: 190
<212> TYPE: PRT
<213> ORGANISM: Artificial Sequence
<220> FEATURE:
<223> OTHER INFORMATION: Novel Sequence

<400> SEQUENCE: 1

Met Glu Asn Arg Trp Gln Val Met Ile Val Trp Gln Val Asp Arg Met
1               5                   10                  15

Arg Ile Arg Thr Trp Asn Ser Leu Val Lys His His Met Tyr Val Ser
            20                  25                  30

Lys Lys Ala Arg Trp Phe Tyr Arg His His Tyr Glu Ser Pro His Pro
        35                  40                  45

Lys Val Ser Ser Glu Val His Ile Pro Leu Gly Asp Ala Arg Leu Glu
    50                  55                  60

Thr Thr Thr Tyr Trp Gly Leu His Gly Glu Arg Asp Trp His Leu Gly
65                  70                  75                  80

Gln Gly Val Ser Ile Glu Trp Arg Lys Arg Arg Tyr Ser Thr Gln Val
            85                  90                  95

Asp Pro Asp Leu Ala Asp Gln Leu Ile His Leu Tyr Tyr Phe Asp Cys
            100                 105                 110

Phe Ser Glu Ser Ala Ile Arg Lys Ala Ile Leu Gly Tyr Arg Val Ser
            115                 120                 125

Pro Arg Cys Glu Tyr Gln Ala Gly His Asn Lys Val Gly Ser Leu Gln
    130                 135                 140

Tyr Leu Ala Leu Ala Ala Leu Ile Thr Pro Lys Lys Ile Lys Pro Pro
145                 150                 155                 160

Leu Pro Ser Val Arg Lys Leu Thr Glu Asp Arg Trp Asn Lys Pro Gln
            165                 170                 175

Lys Thr Lys Gly His Arg Gly Ser His Thr Met Asn Gly His
            180                 185                 190

<210> SEQ ID NO 2
<211> LENGTH: 26
<212> TYPE: DNA
<213> ORGANISM: Artificial Sequence
<220> FEATURE:
<223> OTHER INFORMATION: Novel Sequence

<400> SEQUENCE: 2
gaaagcttat ggaaaacaga tggcag                                      26

<210> SEQ ID NO 3

```
<211> LENGTH: 23
<212> TYPE: DNA
<213> ORGANISM: Artificial Sequence
<220> FEATURE:
<223> OTHER INFORMATION: Novel Sequence

<400> SEQUENCE: 3
gcaaagcttt cattgtatgg ctc                                          23

<210> SEQ ID NO 4
<211> LENGTH: 190
<212> TYPE: PRT
<213> ORGANISM: Artificial Sequence
<220> FEATURE:
<223> OTHER INFORMATION: Novel Sequence

<400> SEQUENCE: 4
```

Met Glu Asn Arg Trp Gln Val Ile Ile Val Trp Gln Val Asp Arg Met
1               5                   10                  15

Arg Ile Arg Thr Trp Asn Ser Leu Val Lys Tyr His Met Tyr Ser Lys
            20                  25                  30

Lys Ala Arg Glu Trp Phe Tyr His His Tyr Gln Ser Pro His Pro Lys
        35                  40                  45

Val Ser Ser Glu Val His Ile Pro Leu Glu Asp Ala Arg Leu Glu Ile
    50                  55                  60

Thr Ser Phe Trp Gly Leu His Thr Gly Glu Arg Asp Trp His Leu Gly
65                  70                  75                  80

Gln Gly Val Ser Ile Glu Trp Arg Lys Arg Tyr Ser Thr His Val
                85                  90                  95

Asp Pro Asp Leu Ala Asp Gln Leu Ile His Leu Tyr Tyr Phe Asp Cys
            100                 105                 110

Phe Ser Glu Ser Ala Ile Arg Lys Ala Ile Leu Gly His Arg Val Ser
        115                 120                 125

Pro Arg Cys Glu Tyr Arg Ala Gly His Ser Lys Val Gly Ser Leu Gln
    130                 135                 140

Tyr Leu Ala Ile Ala Ala Leu Ile Thr Pro Lys Lys Ile Lys Pro Pro
145                 150                 155                 160

Leu Ala Ser Val Arg Lys Leu Thr Glu Asp Arg Trp Asn Lys Pro Gln
                165                 170                 175

Lys Thr Lys Gly His Arg Gly Ser His Thr Met Asn Gly His
            180                 185                 190

```
<210> SEQ ID NO 5
<211> LENGTH: 192
<212> TYPE: PRT
<213> ORGANISM: Artificial Sequence
<220> FEATURE:
<223> OTHER INFORMATION: Novel Sequence

<400> SEQUENCE: 5
```

Met Glu Asn Arg Trp Gln Val Met Ile Val Trp Gln Val Asp Arg Met
1               5                   10                  15

Arg Ile Arg Thr Trp Asn Ser Leu Val Lys Tyr His Met Tyr Arg Ser
            20                  25                  30

Lys Lys Ala Arg Glu Trp Phe Tyr Arg His His Tyr Gln Ser Pro His
        35                  40                  45

Pro Arg Val Ser Ser Glu Val His Ile Pro Leu Glu Asp Ala Arg Leu
    50                  55                  60

Glu Ile Thr Thr Tyr Trp Gly Leu His Thr Gly Glu Arg Asp Trp His

```
                65                  70                  75                  80
Leu Gly Gln Gly Val Ser Ile Glu Trp Arg Lys Arg Tyr Ser Thr
                    85                  90                  95
Gln Val Asp Pro Asp Leu Ala Asp Gln Leu Ile His Leu Tyr Tyr Phe
                100                 105                 110
Asp Cys Phe Ser Glu Ser Ala Ile Arg Lys Ala Ile Leu Gly His Arg
            115                 120                 125
Val Ser Pro Arg Cys Glu Tyr Arg Ala Gly His Ser Lys Val Gly Ser
        130                 135                 140
Leu Gln Tyr Leu Ala Ile Ala Ala Leu Ile Thr Pro Lys Lys Ile Lys
145                 150                 155                 160
Pro Pro Leu Pro Ser Val Arg Lys Leu Thr Glu Asp Arg Trp Asn Lys
                165                 170                 175
Pro Gln Lys Thr Lys Gly His Arg Gly Ser His Thr Met Asn Gly His
                180                 185                 190
```

<210> SEQ ID NO 6
<211> LENGTH: 192
<212> TYPE: PRT
<213> ORGANISM: Artificial Sequence
<220> FEATURE:
<223> OTHER INFORMATION: Novel Sequence

<400> SEQUENCE: 6

```
Met Glu Asn Arg Trp Gln Val Met Ile Val Trp Gln Val Asp Arg Met
1               5                   10                  15
Arg Ile Arg Thr Trp Asn Ser Leu Val Lys Tyr His Met Tyr Arg Ser
                20                  25                  30
Lys Lys Ala Arg Glu Trp Phe Tyr Arg His His Tyr Gln Ser Pro His
            35                  40                  45
Pro Lys Val Ser Ser Glu Val His Ile Pro Leu Glu Asp Ala Arg Leu
        50                  55                  60
Glu Thr Thr Thr Tyr Trp Gly Leu His Thr Gly Glu Arg Asp Trp His
65                  70                  75                  80
Leu Gly Gln Gly Val Ser Ile Glu Trp Arg Lys Arg Tyr Ser Thr
                    85                  90                  95
Gln Val Asp Pro Asp Leu Ala Asp Gln Leu Ile His Leu Tyr Tyr Phe
                100                 105                 110
Asp Cys Phe Ser Glu Ser Ala Ile Arg Lys Ala Ile Leu Gly His Arg
            115                 120                 125
Val Ser Pro Arg Cys Glu Tyr Arg Ala Gly His Ser Lys Val Gly Ser
        130                 135                 140
Leu Gln Tyr Leu Ala Ile Ala Ala Leu Ile Thr Pro Lys Lys Ile Lys
145                 150                 155                 160
Pro Pro Leu Pro Ser Val Arg Lys Leu Thr Glu Asp Arg Trp Asn Lys
                165                 170                 175
Pro Gln Lys Thr Lys Gly His Arg Gly Ser His Thr Met Asn Gly His
                180                 185                 190
```

<210> SEQ ID NO 7
<211> LENGTH: 192
<212> TYPE: PRT
<213> ORGANISM: Artificial Sequence
<220> FEATURE:
<223> OTHER INFORMATION: Novel Sequence

<400> SEQUENCE: 7

```
Met Glu Asn Arg Trp Gln Val Met Ile Val Trp Gln Val Asp Arg Met
1               5                   10                  15

Arg Ile Arg Thr Trp Asn Ser Leu Val Thr Tyr His Met Tyr Arg Ser
                20                  25                  30

Gln Lys Ala Arg Glu Trp Phe Asn Arg His His Tyr His Ser Pro His
            35                  40                  45

Pro Lys Val Ser Ser Glu Val His Ile Pro Leu Glu Asp Ala Arg Leu
        50                  55                  60

Ala Ile Pro Thr Phe Trp Gly Leu His Thr Gly Glu Arg Asp Trp His
65                  70                  75                  80

Leu Gly Gln Gly Val Ser Ile Glu Trp Arg Lys Arg Tyr Ser Thr
                85                  90                  95

Gln Val Asp Pro Asp Leu Ala Asp Gln Leu Ile His Leu Tyr Tyr Phe
                100                 105                 110

Asp Cys Phe Ser Glu Ser Ala Ile Arg Lys Ala Ile Leu Gly His Arg
            115                 120                 125

Val Ser Pro Arg Cys Glu Tyr Arg Ala Gly His Ser Lys Val Gly Ser
        130                 135                 140

Leu Gln Tyr Leu Ala Ile Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
                180                 185                 190
```

<210> SEQ ID NO 8
<211> LENGTH: 192
<212> TYPE: PRT
<213> ORGANISM: Artificial Sequence
<220> FEATURE:
<223> OTHER INFORMATION: Novel Sequence

<400> SEQUENCE: 8

```
Met Glu Asn Arg Trp Gln Val Met Ile Val Trp Gln Val Asp Arg Met
1               5                   10                  15

Arg Ile Arg Thr Trp Asn Ser Leu Val Lys Tyr His Met Tyr Arg Ser
                20                  25                  30

Lys Lys Ala Arg Glu Trp Phe Tyr Arg His His Tyr Gln Ser Pro His
            35                  40                  45

Pro Lys Val Ser Ser Glu Val His Ile Pro Leu Glu Asp Ala Arg Leu
        50                  55                  60

Glu Ile Thr Thr Tyr Trp Gly Leu His Thr Gly Glu Arg Asp Trp His
65                  70                  75                  80

Leu Gly Gln Gly Val Ser Ile Glu Trp Arg Lys Arg Tyr Ser Thr
                85                  90                  95

His Val Asp Pro Asp Leu Ala Asp His Leu Ile His Leu Cys Tyr Phe
                100                 105                 110

Asp Cys Leu Ser Glu Ser Ala Ile Arg Lys Ala Ile Leu Gly His Arg
            115                 120                 125

Val Ser Pro Arg Cys Glu Tyr Arg Ala Gly His Ser Lys Val Gly Ser
        130                 135                 140

Leu Gln Tyr Leu Ala Ile Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175
```

```
Pro Gln Lys Thr Lys Gly His Arg Gly Ser His Thr Met Asn Gly His
            180                 185                 190

<210> SEQ ID NO 9
<211> LENGTH: 192
<212> TYPE: PRT
<213> ORGANISM: Artificial Sequence
<220> FEATURE:
<223> OTHER INFORMATION: Novel Sequence

<400> SEQUENCE: 9

Met Glu Asn Arg Trp Gln Val Met Ile Val Trp Gln Val Asp Arg Met
1               5                   10                  15

Arg Ile Arg Thr Trp Asn Ser Leu Val Lys Tyr His Met Tyr Arg Ser
            20                  25                  30

Lys Lys Ala Arg Glu Trp Phe Tyr Arg His His Tyr Gln Ser Pro His
        35                  40                  45

Pro Lys Val Ser Ser Glu Val His Ile Pro Leu Glu Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Arg Tyr Ser Thr
                85                  90                  95

His Val Asp Pro Asp Leu Ala Asp Gln Leu Ile His Leu Tyr Tyr Phe
            100                 105                 110

Asp Cys Phe Ser Glu Ser Ala Ile Arg Lys Ala Ile Leu Gly His Arg
        115                 120                 125

Val Ser Pro Arg Cys Glu Tyr Arg Ala Gly His Ser Lys Val Gly Ser
    130                 135                 140

Leu Gln Tyr Leu Ala Ile Ala Ala Leu Ile Thr Pro Lys Lys Ile Lys
145                 150                 155                 160

Pro Pro Leu Ala Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

<210> SEQ ID NO 10
<211> LENGTH: 192
<212> TYPE: PRT
<213> ORGANISM: Artificial Sequence
<220> FEATURE:
<223> OTHER INFORMATION: Novel Sequence

<400> SEQUENCE: 10

Met Glu Asn Arg Trp Gln Val Met Ile Val Trp Gln Val Asp Arg Met
1               5                   10                  15

Arg Ile Arg Thr Trp Asn Ser Leu Val Lys Tyr His Met Tyr Arg Ser
            20                  25                  30

Lys Lys Ala Arg Glu Trp Phe Tyr Arg His His Tyr Gln Ser Pro His
        35                  40                  45

Pro Lys Val Ser Ser Glu Val His Ile Pro Leu Glu Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Arg Tyr Ser Thr
                85                  90                  95

Gln Val Asp Pro Asp Leu Ala Asp His Leu Ile His Leu Tyr Tyr Phe
            100                 105                 110
```

Asp Cys Phe Ser Glu Ser Ala Ile Arg Lys Ala Ile Leu Gly His Arg
            115                 120                 125

Val Ser Pro Arg Cys Glu Tyr Arg Ala Gly His Ser Lys Val Gly Ser
        130                 135                 140

Leu Gln Tyr Leu Ala Ile Ala Ala Leu Ile Thr Pro Lys Lys Ile Lys
145                 150                 155                 160

Pro Pro Leu Ala Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

<210> SEQ ID NO 11
<211> LENGTH: 192
<212> TYPE: PRT
<213> ORGANISM: Artificial Sequence
<220> FEATURE:
<223> OTHER INFORMATION: Novel Sequence

<400> SEQUENCE: 11

Met Glu Asn Arg Trp Gln Val Met Ile Val Trp Gln Val Asp Arg Met
1               5                   10                  15

Arg Ile Arg Thr Trp Asn Ser Leu Val Lys Tyr His Met Tyr Arg Ser
            20                  25                  30

Lys Lys Ala Arg Glu Trp Phe Tyr Arg His His Tyr Gln Ser Pro His
        35                  40                  45

Pro Lys Val Ser Ser Glu Val His Ile Pro Leu Glu Asp Ala Arg Leu
    50                  55                  60

Val Ile Thr Thr Phe Trp Gly Leu His Thr Gly Glu Arg Asp Trp His
65                  70                  75                  80

Leu Gly Gln Gly Val Ser Ile Glu Trp Arg Lys Arg Arg Tyr Ser Thr
                85                  90                  95

His Val Asp Pro Asp Leu Ala Asp Gln Leu Ile His Leu Tyr Tyr Phe
            100                 105                 110

Asp Cys Phe Ser Glu Ser Ala Ile Arg Lys Ala Ile Leu Gly His Arg
            115                 120                 125

Val Ser Pro Arg Cys Glu Tyr Arg Ala Gly His Ser Lys Val Gly Ser
        130                 135                 140

Leu Gln Tyr Leu Ala Ile Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

<210> SEQ ID NO 12
<211> LENGTH: 192
<212> TYPE: PRT
<213> ORGANISM: Artificial Sequence
<220> FEATURE:
<223> OTHER INFORMATION: Novel Sequence

<400> SEQUENCE: 12

Met Glu Asn Arg Trp Gln Val Met Ile Val Trp Gln Val Asp Arg Met
1               5                   10                  15

Arg Ile Arg Thr Trp Asn Ser Leu Val Lys Tyr His Met Tyr Arg Ser
            20                  25                  30

Lys Lys Ala Arg Glu Trp Phe Asn Arg His His Tyr His Arg Pro His

```
                 35                  40                  45
Pro Lys Val Ser Ser Glu Val His Ile Pro Leu Glu Asp Ala Arg Leu
         50                  55                  60
Glu Ile Thr Thr Phe Trp Gly Leu His Thr Gly Glu Arg Asp Trp His
 65                  70                  75                  80
Leu Gly Gln Gly Val Ser Ile Glu Trp Arg Lys Arg Tyr Ser Thr
                 85                  90                  95
Gln Val Asp Pro Asp Leu Ala Asp Gln Leu Ile His Leu Tyr Tyr Phe
                100                 105                 110
Asp Cys Phe Ser Glu Ser Ala Ile Arg Lys Ala Ile Leu Gly His Arg
                115                 120                 125
Val Ser Pro Arg Cys Glu Tyr Arg Ala Gly His Ser Lys Val Gly Ser
        130                 135                 140
Leu Gln Tyr Leu Ala Ile Ala Ala Leu Ile Thr Pro Lys Lys Ile Lys
145                 150                 155                 160
Pro Pro Leu Pro Ser Val Arg Lys Leu Thr Glu Asp Arg Trp Asn Lys
                165                 170                 175
Pro Gln Lys Thr Lys Gly His Arg Gly Ser His Thr Met Asn Gly His
                180                 185                 190

<210> SEQ ID NO 13
<211> LENGTH: 192
<212> TYPE: PRT
<213> ORGANISM: Artificial Sequence
<220> FEATURE:
<223> OTHER INFORMATION: Novel Sequence

<400> SEQUENCE: 13

Met Glu Asn Arg Trp Gln Val Met Ile Val Trp Gln Val Asp Arg Met
 1               5                  10                  15
Arg Ile Arg Thr Trp Asn Ser Leu Val Lys Tyr His Met Tyr Arg Ser
                20                  25                  30
Gln Lys Glu Arg Glu Trp Phe Asn Arg His His Tyr His Ser Pro His
                35                  40                  45
Pro Glu Gln Ser Ser Thr Ala His Ile Pro Leu Val Asp Gly Arg Leu
         50                  55                  60
Glu Lys Ile Ala Val Trp Ser Leu Asp Thr Gly Glu Gly Val Trp His
 65                  70                  75                  80
Arg Gly His Arg Val Ser Ile Glu Trp Arg Lys Arg Tyr Ser Thr
                 85                  90                  95
Gln Val Asp Pro Asp Leu Val Asp Gln Leu Ile His Leu Tyr Tyr Phe
                100                 105                 110
Asp Cys Phe Ser Glu Ser Ala Ile Arg Lys Ala Ile Leu Gly His Arg
                115                 120                 125
Val Ser Pro Arg Cys Glu Tyr Arg Ala Gly His Ser Lys Val Gly Ser
        130                 135                 140
Leu Gln Tyr Leu Ala Ile Ala Ala Leu Ile Thr Pro Lys Lys Ile Lys
145                 150                 155                 160
Pro Pro Leu Pro Ser Val Arg Lys Leu Thr Glu Asp Arg Trp Asn Lys
                165                 170                 175
Pro Gln Lys Thr Lys Gly His Arg Gly Ser His Thr Met Asn Gly His
                180                 185                 190

<210> SEQ ID NO 14
<211> LENGTH: 192
<212> TYPE: PRT
```

```
<213> ORGANISM: Artificial Sequence
<220> FEATURE:
<223> OTHER INFORMATION: Novel Sequence

<400> SEQUENCE: 14
```

Met Glu Asn Arg Trp Gln Val Met Ile Val Trp Gln Val Asp Arg Met
1               5                   10                  15

Arg Ile Arg Thr Trp Asn Ser Leu Val Lys His His Met Tyr Val Ser
            20                  25                  30

Lys Lys Ala Lys Lys Trp Phe Tyr Arg His His Tyr Glu Ser Pro His
        35                  40                  45

Pro Lys Val Ser Ser Thr Ala His Ile Pro Leu Gly Asp Gly Arg Leu
    50                  55                  60

Glu Lys Thr Ala Val Trp Ser Leu Gln Ala Gly Asp Gly Val Trp His
65                  70                  75                  80

Arg Gly His Pro Val Ser Ile Glu Trp Arg Lys Arg Tyr Ser Thr
                85                  90                  95

Gln Val Asp Pro Asp Leu Val Asp Gln Leu Ile His Leu Tyr Tyr Phe
                100                 105                 110

Asp Cys Phe Ser Glu Ser Ala Ile Arg Lys Ala Ile Leu Gly Tyr Arg
            115                 120                 125

Val Ser Pro Arg Cys Glu Tyr Gln Ala Gly His Asn Lys Val Gly Ser
130                 135                 140

Leu Gln Tyr Leu Ala Leu Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

```
<210> SEQ ID NO 15
<211> LENGTH: 191
<212> TYPE: PRT
<213> ORGANISM: Artificial Sequence
<220> FEATURE:
<223> OTHER INFORMATION: Novel Sequence

<400> SEQUENCE: 15
```

Met Glu Asn Arg Trp Gln Val Met Ile Val Trp Gln Val Asp Arg Met
1               5                   10                  15

Arg Ile Arg Ala Trp Asn Ser Leu Val Lys His His Met Tyr Val Ser
            20                  25                  30

Lys Lys Ala Arg Thr Trp Phe Ser Arg His His Tyr Gly Ser Pro His
        35                  40                  45

Pro Lys Val Cys Ser Glu Val His Ile Pro Leu Gly Asp Ala Arg Leu
    50                  55                  60

Val Ile Thr Thr Tyr Trp Ser Leu His Ala Gly Glu Asp Trp His Val
65                  70                  75                  80

Gly Gln Arg Val Ser Ile Glu Trp Arg Lys Arg Arg Tyr Ser Thr Gln
                85                  90                  95

Val Asp Pro Asp Leu Ala Asp Gln Leu Ile His Leu Tyr Tyr Phe Asp
                100                 105                 110

Cys Phe Ser Glu Ser Ala Ile Arg Lys Ala Ile Leu Gly Tyr Arg Val
        115                 120                 125

Ser Pro Arg Cys Glu Tyr Gln Ala Gly His Asn Lys Val Gly Ser Leu
130                 135                 140

```
Gln Tyr Leu Ala Leu Ala Ala Leu Ile Thr Pro Lys Lys Ile Lys Pro
145                 150                 155                 160

Pro Leu Pro Ser Val Arg Lys Leu Thr Glu Asp Arg Trp Asn Lys Pro
            165                 170                 175

Gln Lys Thr Lys Gly His Arg Gly Ser His Thr Met Asn Gly His
        180                 185                 190

<210> SEQ ID NO 16
<211> LENGTH: 192
<212> TYPE: PRT
<213> ORGANISM: Artificial Sequence
<220> FEATURE:
<223> OTHER INFORMATION: Novel Sequence

<400> SEQUENCE: 16

Met Glu Asn Arg Trp Gln Val Met Ile Val Trp Gln Val Asp Arg Met
1               5                   10                  15

Arg Ile Arg Ala Trp Asn Ser Leu Val Lys His His Thr Tyr Phe Ser
            20                  25                  30

Lys Lys Ala Lys Lys Trp Phe Tyr Arg His His Tyr Glu Ser Pro His
        35                  40                  45

Pro Asn Val Ser Ser Glu Val His Ile Pro Leu Gly Asp Ala Arg Leu
    50                  55                  60

Val Thr Thr Pro Tyr Trp Gly Leu His Gly Glu Arg Asp Trp Tyr
65                  70                  75                  80

Leu Ala Gln Gly Val Ser Ile Glu Trp Arg Lys Arg Tyr Ser Thr
                85                  90                  95

Gln Val Asp Pro Asp Leu Ala Asp Gln Leu Ile His Leu Tyr Tyr Phe
            100                 105                 110

Asp Cys Phe Ser Glu Ser Ala Ile Arg Lys Ala Ile Leu Gly Tyr Arg
            115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

<210> SEQ ID NO 17
<211> LENGTH: 192
<212> TYPE: PRT
<213> ORGANISM: Artificial Sequence
<220> FEATURE:
<223> OTHER INFORMATION: Novel Sequence

<400> SEQUENCE: 17

Met Glu Asn Arg Trp Glu Val Met Ile Val Trp Glu Val Asp Arg Met
1               5                   10                  15

Arg Ile Arg Ala Trp Asn Ser Leu Val Lys His His Met Tyr Val Ser
            20                  25                  30

Lys Lys Ala Lys Lys Trp Phe Tyr Arg His His Tyr Glu Ser Pro His
        35                  40                  45

Pro Lys Val Ser Ser Glu Val His Ile Pro Leu Gly Asp Ala Arg Leu
    50                  55                  60

Val Ile Thr Thr Tyr Trp Gly Leu His Ala Gly Glu Arg Asp Trp His
65                  70                  75                  80
```

-continued

Leu Gly Gln Gly Val Ser Ile Glu Trp Arg Lys Arg Tyr Ser Thr
                85                  90                  95

Gln Val Asp Pro Asp Leu Ala Asp Gln Leu Ile His Leu Tyr Tyr Phe
            100                 105                 110

Asp Cys Phe Ser Glu Ser Ala Ile Arg Lys Ala Ile Leu Gly Tyr Arg
            115                 120                 125

Val Ser Pro Arg Cys Glu Tyr Gln Ala Gly His Asn Lys Val Gly Ser
            130                 135                 140

Leu Gln Tyr Leu Ala Leu Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
                180                 185                 190

<210> SEQ ID NO 18
<211> LENGTH: 192
<212> TYPE: PRT
<213> ORGANISM: Artificial Sequence
<220> FEATURE:
<223> OTHER INFORMATION: Novel Sequence

<400> SEQUENCE: 18

Met Glu Asn Arg Trp Gln Val Met Ile Val Trp Gln Val Asp Arg Met
1               5                   10                  15

Arg Ile Arg Ala Trp Asn Ser Leu Val Lys His His Met Tyr Val Ser
            20                  25                  30

Lys Asn Ala Lys Lys Trp Phe Tyr Arg His His Tyr Asp Ser Pro His
        35                  40                  45

Pro Val Gln Ser Ser Thr Ala His Ile Pro Leu Gly Asp Gly Arg Leu
    50                  55                  60

Gln Lys Ile Ala Phe Trp Ser Leu Asp Ala Gly Glu Arg Asp Trp His
65                  70                  75                  80

Leu Gly Gln Gly Val Ser Ile Glu Trp Arg Lys Arg Tyr Ser Thr
                85                  90                  95

Gln Val Asp Pro Asp Leu Ala Asp Gln Leu Ile His Leu Tyr Tyr Phe
            100                 105                 110

Asp Cys Phe Ser Glu Ser Ala Ile Arg Lys Ala Ile Leu Gly Tyr Arg
            115                 120                 125

Val Ser Pro Arg Cys Glu Tyr Gln Ala Gly His Asn Lys Val Gly Ser
            130                 135                 140

Leu Gln Tyr Leu Ala Leu Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Arg His Thr Met Asn Gly His
                180                 185                 190

<210> SEQ ID NO 19
<211> LENGTH: 192
<212> TYPE: PRT
<213> ORGANISM: Artificial Sequence
<220> FEATURE:
<223> OTHER INFORMATION: Novel Sequence

<400> SEQUENCE: 19

Met Glu Asn Arg Trp Gln Val Met Ile Val Trp Gln Val Asp Arg Met

-continued

```
                1               5                  10                 15
Arg Ile Arg Ala Trp Asn Ser Leu Val Lys His His Met Tyr Val Ser
                20                 25                 30

Lys Lys Ala Lys Lys Trp Phe Tyr Arg His His Tyr Asp Ser Pro His
                35                 40                 45

Pro Lys Val Ser Ser Glu Val His Ile Pro Leu Gly Asp Ala Arg Leu
                50                 55                 60

Glu Thr Thr Thr Tyr Trp Gly Leu His Ala Gly Glu Arg Asp Trp His
65                   70                 75                 80

Leu Gly Gln Gly Val Ser Ile Glu Trp Arg Lys Arg Tyr Ser Thr
                    85                 90                 95

His Val Asp Pro Asp Leu Ala Asp Gln Leu Ile His Leu Tyr Tyr Phe
                    100                105                110

Asp Cys Phe Ser Glu Ser Ala Ile Arg Lys Ala Ile Leu Gly Tyr Arg
                    115                120                125

Val Ser Pro Arg Cys Glu Tyr Gln Ala Gly His Asn Lys Val Gly Ser
                    130                135                140

Leu Gln Tyr Leu Ala Leu Ala Ala Leu Ile Thr Pro Lys Lys Ile Lys
145                 150                155                160

Pro Pro Leu Pro Ser Val Arg Lys Leu Thr Glu Asp Arg Trp Asn Lys
                    165                170                175

Pro Gln Lys Thr Lys Gly His Arg Gly Ser His Thr Met Asn Gly His
                    180                185                190
```

<210> SEQ ID NO 20
<211> LENGTH: 192
<212> TYPE: PRT
<213> ORGANISM: Artificial Sequence
<220> FEATURE:
<223> OTHER INFORMATION: Novel Sequence

<400> SEQUENCE: 20

```
Met Glu Asn Arg Trp Gln Val Met Ile Val Trp Gln Val Asp Arg Met
1               5                  10                 15

Thr Ile Arg Ala Trp Asn Ser Leu Val Lys His His Met Tyr Val Ser
                20                 25                 30

Lys Lys Ala Lys Lys Trp Phe Tyr Arg His His Tyr Glu Ser Pro His
                35                 40                 45

Pro Lys Val Ser Ser Glu Val His Ile Pro Leu Gly Asp Ala Arg Leu
                50                 55                 60

Val Ile Thr Thr Tyr Trp Gly Leu His Ala Gly Glu Arg Asp Trp His
65                  70                 75                 80

Leu Gly Gln Gly Val Ser Ile Glu Trp Arg Lys Arg Arg Tyr Ser Thr
                    85                 90                 95

Gln Val Asp Pro Asp Leu Ala Asp Gln Leu Thr His Leu Tyr Tyr Phe
                    100                105                110

Asp Cys Phe Ser Glu Ser Ala Ile Arg Lys Ala Ile Leu Gly Tyr Arg
                    115                120                125

Val Ser Pro Arg Cys Glu Tyr Gln Ala Gly His Asn Lys Val Gly Ser
                    130                135                140

Leu Gln Tyr Leu Ala Leu Ala Ala Leu Ile Thr Pro Lys Lys Ile Lys
145                 150                155                160

Pro Pro Leu Pro Ser Val Arg Lys Leu Thr Glu Asp Arg Trp Asn Lys
                    165                170                175

Pro Gln Lys Thr Lys Gly His Arg Gly Ser His Thr Met Asn Gly His
```

```
                      180                 185                 190

<210> SEQ ID NO 21
<211> LENGTH: 188
<212> TYPE: PRT
<213> ORGANISM: Artificial Sequence
<220> FEATURE:
<223> OTHER INFORMATION: Novel Sequence

<400> SEQUENCE: 21

Met Glu Asn Arg Trp Gln Val Met Ile Val Trp Gln Val Asp Arg Met
1               5                   10                  15

Arg Ile Arg Ala Trp Asn Ser Leu Val Lys His His Met Tyr Val Ser
                20                  25                  30

Lys Lys Ala Lys Lys Trp Phe Asn Arg His His Tyr Asp Arg Pro His
            35                  40                  45

Pro Lys Val Ser Ser Glu Val His Ile Pro Leu Gly Asp Ala Arg Leu
        50                  55                  60

Glu Ile Thr Thr Phe Trp Gly Leu His Ala Gly Glu Arg Asp Trp His
65                  70                  75                  80

Leu Gly Gln Arg Val Ser Ile Glu Trp Arg Lys Arg Tyr Ser Thr
                85                  90                  95

Gln Val Asp Pro Asp Leu Ala Asp Gln Leu Thr His Leu Tyr Tyr Phe
                100                 105                 110

Asp Cys Phe Ser Glu Ser Ala Ile Arg Lys Ala Ile Leu Gly Tyr Arg
            115                 120                 125

Val Ser Pro Arg Cys Glu Tyr Gln Ala Gly His Asn Lys Val Gly Ser
        130                 135                 140

Leu Gln Tyr Leu Ala Leu Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly Thr Glu Gly Ala Ile Gln
                180                 185

<210> SEQ ID NO 22
<211> LENGTH: 192
<212> TYPE: PRT
<213> ORGANISM: Artificial Sequence
<220> FEATURE:
<223> OTHER INFORMATION: Novel Sequence

<400> SEQUENCE: 22

Met Glu Asn Arg Trp Gln Val Met Ile Val Trp Gln Val Asp Arg Met
1               5                   10                  15

Arg Ile Arg Ala Trp Asn Ser Leu Val Lys His His Met Phe Val Ser
                20                  25                  30

Lys Lys Ala Lys Lys Trp Phe Tyr Arg His His Tyr Glu Ser Pro His
            35                  40                  45

Pro Lys Val Ser Ser Glu Val His Ile Pro Leu Gly Asp Ala Arg Leu
        50                  55                  60

Glu Ile Thr Thr Phe Trp Gly Leu His Ala Gly Glu Arg Asp Trp His
65                  70                  75                  80

Leu Gly Gln Gly Val Ser Ile Glu Trp Arg Lys Arg Arg Tyr Ser Thr
                85                  90                  95

Gln Val Asp Pro Asp Leu Ala Asp Gln Leu Ile His Leu Tyr Tyr Phe
                100                 105                 110
```

```
Gly Cys Phe Ser Glu Ser Ala Ile Arg Lys Ala Ile Leu Gly Tyr Arg
            115                 120                 125

Val Ser Pro Arg Cys Glu Tyr Gln Ala Gly His Asn Lys Val Gly Ser
        130                 135                 140

Leu Gln Tyr Leu Gly Leu Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

<210> SEQ ID NO 23
<211> LENGTH: 192
<212> TYPE: PRT
<213> ORGANISM: Artificial Sequence
<220> FEATURE:
<223> OTHER INFORMATION: Novel Sequence

<400> SEQUENCE: 23

Met Glu Asn Arg Trp Gln Val Met Ile Val Trp Gln Val Asp Arg Met
1               5                   10                  15

Arg Ile Arg Ala Trp Asn Ser Leu Val Lys His His Met Tyr Val Ser
            20                  25                  30

Lys Lys Ala Lys Lys Trp Phe Tyr Arg His His Tyr Glu Ser Pro His
        35                  40                  45

Pro Gln Val Ser Ser Glu Val His Ile Pro Leu Gly Asp Ala Arg Leu
    50                  55                  60

Glu Ile Thr Thr Tyr Trp Gly Leu His Ala Gly Glu Arg Asp Trp His
65                  70                  75                  80

Leu Gly Gln Gly Val Ser Ile Glu Trp Arg Lys Arg Tyr Ser Thr
                85                  90                  95

Gln Val Asp Pro Asp Leu Ala Asp Gln Leu Ile His Leu Tyr Tyr Phe
            100                 105                 110

Asp Cys Phe Ser Glu Ser Ala Ile Arg Lys Ala Ile Leu Gly Tyr Arg
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

<210> SEQ ID NO 24
<211> LENGTH: 8
<212> TYPE: PRT
<213> ORGANISM: Artificial Sequence
<220> FEATURE:
<223> OTHER INFORMATION: Novel Sequence

<400> SEQUENCE: 24

Ile Glu Trp Arg Lys Lys Arg Tyr
1               5

<210> SEQ ID NO 25
<211> LENGTH: 7
<212> TYPE: PRT
<213> ORGANISM: Artificial Sequence
```

```
<220> FEATURE:
<223> OTHER INFORMATION: Novel Sequence

<400> SEQUENCE: 25

Asp Arg Trp Asn Lys Pro Gln
1               5

<210> SEQ ID NO 26
<211> LENGTH: 6
<212> TYPE: PRT
<213> ORGANISM: Artificial Sequence
<220> FEATURE:
<223> OTHER INFORMATION: Novel Sequence

<400> SEQUENCE: 26

Ser Leu Gln Tyr Leu Ala
1               5

<210> SEQ ID NO 27
<211> LENGTH: 579
<212> TYPE: DNA
<213> ORGANISM: Artificial Sequence
<220> FEATURE:
<223> OTHER INFORMATION: Novel Sequence

<400> SEQUENCE: 27
```

| | | | | | |
|---|---|---|---|---|---|
| atggaaaaca | gatggcaggt | gattattgtg | tggcaggtag | acaggatgag | gattagaaca | 60 |
| tggaacagtt | tagtaaaata | ccatatgtat | tgatcaaaga | aagctaggga | atggttttat | 120 |
| tgacatcact | atcaaagtcc | tcatccaaaa | gtaagttcag | aagtacacat | cccactagag | 180 |
| gatgctagat | tggaaataac | atcattttgg | ggtctgcata | caggagaaag | agactggcat | 240 |
| ttgggtcagg | gagtctccat | agaatggagg | aaaaggagat | atagcacaca | cgtcgaccct | 300 |
| gatctagcag | accaactaat | tcatctgtat | tattttgatt | gttttttcaga | atctgctata | 360 |
| agaaaagcca | tattaggaca | cagagttagt | cctaggtgtg | aatatcgagc | aggacatagc | 420 |
| aaggtaggat | cactacagta | cttggcaata | gcagcattaa | taacaccaaa | aaagataaag | 480 |
| ccaccttttgg | cgagtgtcag | gaaactgaca | gaggatagat | ggaacaagcc | ccagaagacc | 540 |
| aagggccaca | gagggagcca | tacaatgaat | ggacactag | | | 579 |

```
<210> SEQ ID NO 28
<211> LENGTH: 579
<212> TYPE: DNA
<213> ORGANISM: Artificial Sequence
<220> FEATURE:
<223> OTHER INFORMATION: Novel Sequence

<400> SEQUENCE: 28
```

| | | | | | |
|---|---|---|---|---|---|
| atggaaaaca | gatggcaggt | gatgattgtg | tggcaggtag | acaggatgag | gattagaaca | 60 |
| tggaacagtt | tagtaaaata | ccatatgtat | agatcaaaga | aagctaggga | atggttttat | 120 |
| agacatcact | atcaaagtcc | tcatccaaga | gtaagttcag | aagtacacat | cccactagag | 180 |
| gatgctagat | tggaaataac | aacatattgg | ggtctgcata | caggagaaag | agactggcat | 240 |
| ttgggtcagg | gagtctccat | agaatggagg | aaaaggagat | atagcacaca | agtagaccct | 300 |
| gatctagcag | accaactaat | tcatctgtat | tattttgatt | gttttttcaga | atctgctata | 360 |
| agaaaagcca | tattaggaca | cagagttagt | cctaggtgtg | aatatcgagc | aggacatagc | 420 |
| aaggtaggat | cactacagta | cttggcaata | gcagcattaa | taacaccaaa | aaagataaag | 480 |
| ccaccttttgc | cgagtgtcag | gaaactgaca | gaggatagat | ggaacaagcc | ccagaagacc | 540 |

| aagggccaca gagggagcca tacaatgaat ggacactag | 579 |

<210> SEQ ID NO 29
<211> LENGTH: 579
<212> TYPE: DNA
<213> ORGANISM: Artificial Sequence
<220> FEATURE:
<223> OTHER INFORMATION: Novel Sequence

<400> SEQUENCE: 29

| atggaaaaca gatggcaggt gatgattgtg tggcaggtag acaggatgag gattagaaca | 60 |
| tggaacagtt tagtaaaata ccatatgtat agatcaaaga aagctaggga atggttttat | 120 |
| agacatcact atcaaagtcc tcatccaaaa gtaagttcag aagtacacat cccactagag | 180 |
| gatgctagat tggaaataac aacatattgg ggtctgcata caggagaaag agactggcat | 240 |
| ttgggtcagg gagtctccat agaatggagg aaaaggagat atagcacaca agtagaccct | 300 |
| gatctagcag accaactaat tcatctgtat tattttgatt gttttttcaga atctgctata | 360 |
| agaaaagcca tattaggaca cagagttagt cctaggtgtg aatatcgagc aggacatagc | 420 |
| aaggtaggat cactacagta cttggcaata gcagcattaa taacaccaaa aaagataaag | 480 |
| ccacctttgc cgagtgtcag gaaactgaca gaggatagat ggaacaagcc ccagaagacc | 540 |
| aagggccaca gagggagcca tacaatgaat ggacactag | 579 |

<210> SEQ ID NO 30
<211> LENGTH: 579
<212> TYPE: DNA
<213> ORGANISM: Artificial Sequence
<220> FEATURE:
<223> OTHER INFORMATION: Novel Sequence

<400> SEQUENCE: 30

| atggaaaaca gatggcaggt gatgattgtg tggcaggtag acaggatgag gattagaaca | 60 |
| tggaacagtt tagtaacata ccatatgtat agatcacaga aagctaggga atggttttaat | 120 |
| agacatcact atcacagtcc tcatccaaaa gtaagttcag aagtccacat cccactagag | 180 |
| gatgctagat tggcaatacc aacattttgg ggtctgcata caggagaaag agactggcat | 240 |
| ttgggtcagg gagtctccat agaatggagg aaaaggagat atagcacaca agtagaccct | 300 |
| gatctagcag accaactaat tcatctgtat tattttgatt gttttttcaga atctgctata | 360 |
| agaaaagcca tattaggaca cagagttagt cctaggtgtg aatatcgagc aggacatagc | 420 |
| aaggtaggat cactacagta cttggcaata gcagcattaa taacaccaaa aaagataaag | 480 |
| ccacctttgc cgagtgtcag gaaactgaca gaggatagat ggaacaagcc ccagaagacc | 540 |
| aagggccaca gagggagcca tacaatgaat ggacactag | 579 |

<210> SEQ ID NO 31
<211> LENGTH: 579
<212> TYPE: DNA
<213> ORGANISM: Artificial Sequence
<220> FEATURE:
<223> OTHER INFORMATION: Novel Sequence

<400> SEQUENCE: 31

| atggaaaaca gatggcaggt gatgattgtg tggcaggtag acaggatgag gattagaaca | 60 |
| tggaacagtt tagtaaaata ccatatgtat agatcaaaga aagctaggga atggttttat | 120 |
| agacatcact atcaaagtcc tcatccaaaa gtaagttcag aagtccacat cccactagag | 180 |
| gatgctagat tggaaataac aacatattgg ggtctgcata caggagaaag agactggcat | 240 |

```
ttgggtcagg gagtctccat agaatggagg aaaaggagat atagcacaca cgtcgaccct    300
gatctcgcag accacctaat tcatctgtgt tattttgatt gtctttcaga atctgctata    360
agaaaagcca tattaggaca cagagttagt cctaggtgtg aatatcgagc aggacatagc    420
aaggtaggat cactacagta cttggcaata gcagcattaa taacaccaaa aaagataaag    480
ccacctttgc cgagtgtcag gaaactgaca gaggatagat ggaacaagcc ccagaagacc    540
aagggccaca gagggagcca tacaatgaat ggacactag                          579
```

<210> SEQ ID NO 32
<211> LENGTH: 579
<212> TYPE: DNA
<213> ORGANISM: Artificial Sequence
<220> FEATURE:
<223> OTHER INFORMATION: Novel Sequence

<400> SEQUENCE: 32

```
atggaaaaca gatggcaggt gatgattgtg tggcaggtag acaggatgag gattagaaca     60
tggaacagtt tagtaaaata ccatatgtat agatcaaaga aagctaggga atggttttat    120
agacatcact atcaaagtcc tcatccaaaa gtaagttcag aagtacacat cccactagag    180
gatgctagat tggtaataac aacatattgg ggtctgcata caggagaaag agactggcat    240
ttgggtcagg gagtctccat agaatggagg aaaaggagat atagcacaca cgtagaccct    300
gatctagcag accaactaat tcatctgtat tattttgatt gttttcaga atctgctata     360 agaaaagcca tattaggaca cagagttagt cctaggtgtg aatatcgagc aggacatagc    420
aaggtaggat cactacagta cttggcaata gcagcattaa taacaccaaa aaagataaag    480
ccacctttgg cgagtgtcag gaaactgaca gaggatagat ggaacaagcc ccagaagacc    540
aagggccaca gagggagcca tacaatgaat ggacactag                          579
```

<210> SEQ ID NO 33
<211> LENGTH: 579
<212> TYPE: DNA
<213> ORGANISM: Artificial Sequence
<220> FEATURE:
<223> OTHER INFORMATION: Novel Sequence

<400> SEQUENCE: 33

```
atggaaaaca gatggcaggt gatgattgtg tggcaggtag acaggatgag gattagaaca     60
tggaacagtt tagtaaaata ccatatgtat agatcaaaga aagctaggga atggttttat    120
agacatcact atcaaagtcc tcatccaaaa gtaagttcag aagtacacat cccactagag    180
gatgctagat tggtaataac aacatattgg ggtctgcata caggagaaag agactggcat    240
ttgggtcagg gagtctccat agaatggagg aaaaggagat atagcacaca agtagaccct    300
gatctagcag accacctaat tcatctgtat tattttgatt gttttcaga atctgctata     360 agaaaagcca tattaggaca cagagttagt cctaggtgtg aatatcgagc aggacatagc    420
aaggtaggat cactacagta cttggcaata gcagcattaa taacaccaaa aaagataaag    480
ccacctttgg cgagtgtcag gaaactgaca gaggatagat ggaacaagcc ccagaagacc    540
aagggccaca gagggagcca tacaatgaat ggacactag                          579
```

<210> SEQ ID NO 34
<211> LENGTH: 579
<212> TYPE: DNA
<213> ORGANISM: Artificial Sequence
<220> FEATURE:

<223> OTHER INFORMATION: Novel Sequence

<400> SEQUENCE: 34

```
atggaaaaca gatggcaggt gatgattgtg tggcaggtag acaggatgag gattagaaca      60
tggaacagtt tagtaaaata ccatatgtat agatcaaaga aagctaggga atggttttat     120
agacatcact atcaaagtcc tcatccaaaa gtaagttcag aagtacacat cccactagag     180
gatgctagat tggtaataac aacattttgg ggtctgcata caggagaaag agactggcat     240
ttgggtcagg gagtctccat agaatggagg aaaaggagat atagcacaca cgtagaccct     300
gatctagcag accaactaat tcatctgtat tattttgatt gtttttcaga atctgctata     360
agaaaagcca tattaggaca cagagttagt cctaggtgtg aatatcgagc aggacatagc     420
aaggtaggat cactacagta cttggcaata gcagcattaa taacaccaaa aaagataaag     480
ccacctttgc cgagtgtcag gaaactgaca gaggatagat ggaacaagcc ccagaagacc     540
aagggtcaca gagggagcca tacaatgaat ggacactag                            579
```

<210> SEQ ID NO 35
<211> LENGTH: 579
<212> TYPE: DNA
<213> ORGANISM: Artificial Sequence
<220> FEATURE:
<223> OTHER INFORMATION: Novel Sequence

<400> SEQUENCE: 35

```
atggaaaaca gatggcaggt gatgattgtg tggcaggtag acaggatgag gattagaaca      60
tggaacagtt tagtaaaata ccatatgtat agatcaaaga aagctaggga atggttttaat    120
agacatcact atcaccgtcc tcatccaaaa gtaagttcag aagtccacat cccactagag     180
gatgctagat tggaaataac aacattttgg ggtctgcata caggagaaag agactggcat     240
ttgggtcagg gagtctccat agaatggagg aaaaggagat atagcacaca agtagaccct     300
gatctagcag accaactaat tcatctgtat tattttgatt gtttttcaga atctgctata     360
agaaaagcca tattaggaca cagagttagt cctaggtgtg aatatcgagc aggacatagc     420
aaggtaggat cactacagta cttggcaata gcagcattaa taacaccaaa aaagataaag     480
ccacctttgc cgagtgtcag gaaactgaca gaggatagat ggaacaagcc ccagaagacc     540
aagggccaca gagggagcca tacaatgaat ggacactag                            579
```

<210> SEQ ID NO 36
<211> LENGTH: 584
<212> TYPE: DNA
<213> ORGANISM: Artificial Sequence
<220> FEATURE:
<223> OTHER INFORMATION: Novel Sequence

<400> SEQUENCE: 36

```
atggaaaaca gatggcaggt gatgattgtg tggcaggtag acaggatgag gattagaaca      60
tggaacagtt tagtaaaata ccatatgtat tgatcaaaga aagaaagaa agggaatggt     120
tttatagaca tcactatcac agccctcatc cagaacaaag ttcaacagcc cacatcccgc     180
tagtggatgg tagattggaa aaaatagcag tttggagtct ggatacagga gatggcgtct     240
ggcacagggg gcatcgagtc tccatagaat ggaggaaaag gagatatagc acacaagtag     300
accctgatct agtagaccaa ctaattcatc tgtattattt tgattgtttt tcagaatctg     360
ctataagaaa agccatatta ggacacagag ttagtcctag gtgtgaatat cgagcaggac     420
atagcaaggt aggatcacta cagtacttgg caatagcagc attaataaca ccaaaaaaga     480
```

```
taaagccacc tttgccgagt gtcaggaaac tgacagagga tagatggaac aagccccaga      540
agaccaaggg ccacagaggg agccatacaa tgaatggaca ctag                      584
```

<210> SEQ ID NO 37
<211> LENGTH: 579
<212> TYPE: DNA
<213> ORGANISM: Artificial Sequence
<220> FEATURE:
<223> OTHER INFORMATION: Novel Sequence

<400> SEQUENCE: 37

```
atggaaaaca gatggcaggt gatgattgtg tggcaagtag acaggatgag gattagaaca       60
tggaacagtt tagtaaaaca ccatatgtat gtttcaaaga aagctaagaa atggttttat      120
agacatcact atgaaagccc tcatccaaaa gtaagttcaa cagcccacat cccgctaggg      180
gatggtagat tggagaaaac agcagtttgg agtctgcagg caggagatgg agtctggcac      240 aggggcatc cagtctccat agaatggagg aaaaggagat atagcacaca gtagaccct       300 gatttggtag accaactaat tcatctgtat tattttgatt gttttcaga atctgctata      360 agaaaagcca tattaggata tagagttagt cctaggtgtg aataccaagc aggacataat      420
aaggtaggat ctctacagta cttggcacta gcagcattaa taacaccaaa gaagataaag      480
ccacctttgc ctagtgttag gaaactgaca gaggatagat ggaacaagcc ccagaagacc      540
aagggccaca gagggagcca tacaatgaat ggacactag                             579
```

<210> SEQ ID NO 38
<211> LENGTH: 579
<212> TYPE: DNA
<213> ORGANISM: Artificial Sequence
<220> FEATURE:
<223> OTHER INFORMATION: Novel Sequence

<400> SEQUENCE: 38

```
atggaaaaca gatggcaggt gatgattgtg tggcaagtag acaggatgag gattagagca       60
tggaacagtt tagtaaaaca ccatatgtat gtttcaaaga aagctaggac atggttttct      120
agacatcact atgaagccc tcatccaaaa gtatgttcag aagtacacat cccactaggg       180
gatgctagat tggtgataac aacatattgg agtctgcatg caggagaatg agactggcat      240
gtgggtcaga gagtctccat agaatggagg aaaaggagat atagcacaca gtagaccct      300 gacttggcag accaactaat tcatctgtat tattttgatt gttttcaga atctgctata      360 agaaaagcca tattaggata tagagttagt cctaggtgtg aataccaagc aggacataat      420
aaggtaggat ctctacagta cttggcacta gcagcattaa taacaccaaa gaagataaag      480
ccacctttgc ctagtgtgag gaaactgaca gaggatagat ggaacaagcc ccagaagacc      540
aagggccaca gagggagcca tacaatgaat ggacactag                             579
```

<210> SEQ ID NO 39
<211> LENGTH: 579
<212> TYPE: DNA
<213> ORGANISM: Artificial Sequence
<220> FEATURE:
<223> OTHER INFORMATION: Novel Sequence

<400> SEQUENCE: 39

```
atggaaaaca gatggcaggt gatgattgtg tggcaagtag acaggatgag gattagagca       60
tggaacagtt tagtaaaaca ccatatttat ttttcaaaga aagctaagaa atggttttat      120
```

```
agacatcact atgaaagccc tcatccaaac gtaagttcag aagtacacat cccactaggg    180
gatgctagat tggtgacaac accatattgg ggtctgcatg gaggagaaag agactggtat    240
ctggctcagg gagtctccat agaatggagg aaaaggagat atagcacaca agtagaccct    300
gacctggcag accaactaat tcatctgtat tattttgatt gttttttcaga atctgctata   360 agaaaagcca tattaggata tagagttagt cctaggtgtg aataccaagc aggacataat    420
aaggtaggat ctctacagta cttggcacta gcagcattaa taacaccaaa gaagataaag    480
ccacctttgc ctagtgtgag gaaactgaca gaggatagat ggaacaagcc ccagaagacc    540
aagggccaca gagggagcca tacaatgaat ggacactag                           579

<210> SEQ ID NO 40
<211> LENGTH: 579
<212> TYPE: DNA
<213> ORGANISM: Artificial Sequence
<220> FEATURE:
<223> OTHER INFORMATION: Novel Sequence

<400> SEQUENCE: 40
atggaaaaca gatgggaggt gatgattgtg tgggaagtag acaggatgag gattagagca    60
tggaacagtt tagtaaaaca ccatatgtat gtttcaaaga aagctaagaa atggttttat    120
agacatcact atgaaagccc tcatccaaaa gtaagttcag aagtacacat cccactaggg    180
gatgctagat tggtgataac aacatattgg ggtctgcatg caggagaaag agactggcat    240
ttgggtcagg gagtctccat agaatggagg aaaaggagat atagcacaca agtagaccct    300
gacctggcag accaactaat tcatctgtat tattttgatt gttttttcaga atctgctata   360 agaaaagcca tattaggata tagagttagt cctaggtgtg aataccaagc aggacataat    420
aaggtaggat ctctacagta cttggcacta gcagcattaa taacaccaaa gaagataaag    480
ccacctttgc ctagtgtgag gaaactgaca gaggatagat ggaacaagcc ccagaagacc    540
aagggccaca gagggagcca tacaatgaat ggacactag                           579

<210> SEQ ID NO 41
<211> LENGTH: 579
<212> TYPE: DNA
<213> ORGANISM: Artificial Sequence
<220> FEATURE:
<223> OTHER INFORMATION: Novel Sequence

<400> SEQUENCE: 41
atggaaaaca gatggcaggt gatgattgtg tggcaagtag acaggatgag gattagagca    60
tggaacagtt tagtaaaaca ccatatgtat gtttcaaaga acgctaagaa atggttttat    120
cgacatcact atgacagccc tcatccagtc caaagttcaa cagcccacat cccgctaggg    180
gatggtagat tgcagaaaat agcatttttgg agtctggatg caggagaaag agactggcat    240
ttgggtcagg gagtctccat agaatggagg aaaaggagat atagcacaca agtagaccct    300
gacctggcag accaactaat tcatctgtat tattttgatt gttttttcaga atctgctata   360 agaaaagcca tattaggata tagagttagt cctaggtgtg aataccaagc aggacataat    420
aaggtaggat ctctacagta cttggcacta gcagcattaa taacaccaaa gaagataaag    480
ccacctttgc ctagtgtgag gaaactgaca gaggatagat ggaacaagcc ccagaagacc    540 aagggggcaca gagggaggca tacaatgaat ggacactag                          579

<210> SEQ ID NO 42
<211> LENGTH: 579
```

```
<212> TYPE: DNA
<213> ORGANISM: Artificial Sequence
<220> FEATURE:
<223> OTHER INFORMATION: Novel Sequence

<400> SEQUENCE: 42
atggaaaaca gatggcaggt gatgattgtg tggcaagtag acaggatgag gattagagca    60
tggaacagtt tagtaaaaca ccatatgtat gtttcaaaga aagctaagaa atggttttat   120
agacatcact atgacagccc tcatccaaaa gtaagttcag aagtacacat cccactaggg   180
gatgctagat tggagataac aacatattgg ggtctgcatg caggagaaag agactggcat   240
ttgggtcagg gagtctccat agaatggagg aaaaggagat atagcacaca cgtagaccct   300
gacctggcag accaactaat tcatctgtat tattttgatt gttttttcaga atctgctata   360 agaaaagcca tattaggata tagagttagt cctaggtgtg aataccaagc aggacataat   420
aaggtaggat ctctacagta cttggcacta gcagcattaa taacaccaaa gaagataaag   480
ccacctttgc ctagtgtgag gaaactgaca gaggatagat ggaacaagcc ccagaagacc   540
aagggccaca gagggagcca tacaatgaat ggacactag                          579

<210> SEQ ID NO 43
<211> LENGTH: 579
<212> TYPE: DNA
<213> ORGANISM: Artificial Sequence
<220> FEATURE:
<223> OTHER INFORMATION: Novel Sequence

<400> SEQUENCE: 43
atggaaaaca gatggcaggt gatgattgtg tggcaagtag acaggatgac gattagagca    60
tggaacagtt tagtaaaaca ccatatgtat gtttcaaaga aagctaagaa atggttttat   120
agacatcact atgaaagccc tcatccaaaa gtaagttcag aagtacacat cccactaggg   180
gatgctagat tggtgataac aacatattgg ggtctgcatg caggagaaag agactggcat   240
ttgggtcagg gagtctccat agaatggagg aaaaggagat atagcacaca agtagaccct   300
gacttggcag accaactaac tcatctgtat tattttgatt gttttttcaga atctgctata   360 agaaaagcca tattaggata tagagttagt cctaggtgtg aataccaagc aggacataat   420
aaggtaggat ctctacagta cttggcacta gcagcattaa taacaccaaa gaagataaag   480
ccacctttgc ctagtgtgag gaaactgaca gaggatagat ggaacaagcc ccagaagacc   540
aagggccaca gagggagcca tacaatgaat ggacactag                          579

<210> SEQ ID NO 44
<211> LENGTH: 578
<212> TYPE: DNA
<213> ORGANISM: Artificial Sequence
<220> FEATURE:
<223> OTHER INFORMATION: Novel Sequence

<400> SEQUENCE: 44
atggaaaaca gatggcaggt gatgattgtg tggcaagtag acaggatgag gattagagca    60
tggaacagtt tagtaaaaca ccatatgtat gtttcaaaga aagctaagaa atggtttaat   120
agacatcact atgaccgccc tcatccaaaa gtaagttcag aagtccacat cccactaggg   180
gatgctagat tggagataac aacattttgg ggtctgcatg caggagaaag agactggcat   240
ttgggtcagc gagtctccat agaatggagg aaaaggagat atagcacaca agtagaccct   300
gacttggcag accaactaac tcatctgtat tattttgatt gttttttcaga atctgctata   360
```

```
agaaaagcca tattaggata tagagttagt cctaggtgtg aataccaagc aggacataat      420
aaggtaggat ctctacagta cttggcacta gcagcattaa taacaccaaa gaagataaag      480
ccacctttgc ctagtgtgag gaaactgaca gaggatagat ggaacaagcc ccagaagacc      540
aagggcacag agggagccat acaatgaatg gacactag                             578

<210> SEQ ID NO 45
<211> LENGTH: 579
<212> TYPE: DNA
<213> ORGANISM: Artificial Sequence
<220> FEATURE:
<223> OTHER INFORMATION: Novel Sequence

<400> SEQUENCE: 45
atggaaaaca gatggcaggt gatgattgtg tggcaagtag acaggatgag gattagagca       60
tggaacagtt tagtaaaaca ccatatgttt gtttcaaaga aagctaagaa atggttttat      120
agacatcact atgaaagccc tcatccaaaa gtaagttcag aagtacacat cccactaggg      180
gatgctagat tggagataac aacatttggg ggtctgcatg caggagaaag agactggcat      240
ttgggtcagg gagtctccat agaatggagg aaaaggagat atagcacaca gtagaccct      300 gacctggcag accaactaat tcatctgtat tattttggtt gttttcaga atctgctata      360 agaaaagcca tattaggata tagagttagt cctaggtgtg aataccaagc aggacataat      420
aaggtaggat ctctacagta cttgggacta gcagcattaa taacaccaaa gaagataaag      480
ccacctttgc ctagtgtgag gaaactgaca gaggatagat ggaacaagcc ccagaagacc      540
aagggccaca gagggagcca tacaatgaat ggacactag                             579

<210> SEQ ID NO 46
<211> LENGTH: 579
<212> TYPE: DNA
<213> ORGANISM: Artificial Sequence
<220> FEATURE:
<223> OTHER INFORMATION: Novel Sequence

<400> SEQUENCE: 46
atggaaaaca gatggcaggt gatgattgtg tggcaagtag acaggatgag gattagagca       60
tggaacagtt tagtaaaaca ccatatgtat gtttcaaaga aagctaagaa atggttttat      120
agacatcact atgaaagccc tcatccacaa gtaagttcag aagtacacat cccactaggg      180
gatgctagat tggagataac aacatattgg ggtctgcatg caggagaaag agactggcat      240
ttgggtcagg gagtctccat agaatggagg aaaaggagat atagcacaca gtagaccct      300 gacctggcag accaactaat tcatctgtat tattttgatt gttttcaga atctgctata      360 agaaaagcca tattaggata tagagttagt cctaggtgtg aataccaagc aggacataat      420
aaggtaggat ctctacagta cttggcacta gcagcattaa taacaccaaa gaagataaag      480
ccacctttgc ctagtgtgag gaaactgaca gaggatagat ggaacaagcc ccagaagacc      540
aagggccaca gagggagcca tacaatgaat ggacactag                             579
```